(12) United States Patent
MacKeil et al.

(10) Patent No.: US 10,702,282 B2
(45) Date of Patent: Jul. 7, 2020

(54) DEVICES AND METHODS FOR COMPRESSING A DIGIT TO FACILITATE REMOVAL OF A RING

(71) Applicants: Brad MacKeil, Fletcher's Lake (CA); Mason Landry, Halifax (CA); Callum Thompson, Halifax (CA); Patrick Hennessey, Dartmouth (CA); Kevin Spencer, Bedford (CA); Robert Nicolas Pratt, Ottawa (CA); William Dicke, Ottawa (CA); Michael Brown, Ottawa (CA)

(72) Inventors: Brad MacKeil, Fletcher's Lake (CA); Mason Landry, Halifax (CA); Callum Thompson, Halifax (CA); Patrick Hennessey, Dartmouth (CA); Kevin Spencer, Bedford (CA); Robert Nicolas Pratt, Ottawa (CA); William Dicke, Ottawa (CA); Michael Brown, Ottawa (CA)

(73) Assignee: RING RESCUE INCORPORATED, Bedford (CA)

( * ) Notice: Subject to any disclaimer, the term of this patent is extended or adjusted under 35 U.S.C. 154(b) by 0 days.

(21) Appl. No.: 16/361,526

(22) Filed: Mar. 22, 2019

(65) Prior Publication Data

US 2019/0298391 A1 Oct. 3, 2019

Related U.S. Application Data

(63) Continuation of application No. PCT/CA2019/050299, filed on Mar. 12, 2019.
(Continued)

(30) Foreign Application Priority Data

Mar. 29, 2018 (CA) ....................... 2999658

(51) Int. Cl.
*A61B 17/135* (2006.01)
*A61B 17/132* (2006.01)

(52) U.S. Cl.
CPC ........ *A61B 17/135* (2013.01); *A61B 17/1322* (2013.01)

(58) Field of Classification Search
CPC ............. A61B 17/132; A61B 17/1322; A61H 9/0078; A61F 5/0118; A61F 5/10; A61F 2005/415; A63B 23/16
(Continued)

(56) References Cited

U.S. PATENT DOCUMENTS 4,013,069 A 3/1977 Hasty
4,135,299 A 1/1979 Moriarty
(Continued)

FOREIGN PATENT DOCUMENTS

CA 1293624 C 12/1991
CA 2080526 A1 4/1993
(Continued)

OTHER PUBLICATIONS

International Search Report and Written Opinion dated Aug. 6, 2019 in corresponding International Patent Application No. PCT/CA2019/050299 (12 pages).
(Continued)

*Primary Examiner* — Diane D Yabut
*Assistant Examiner* — Majid Jamialahmadi
(74) *Attorney, Agent, or Firm* — Bereskin & Parr LLP

(57) ABSTRACT

A compression device for freeing a ring trapped on a digit includes a rigid outer body. The rigid outer body includes a digit cavity extending from a cavity opening at a body proximal end of the body towards a body distal end of the body, a fluid inlet, and a fluid flow path fluidly connecting the fluid inlet to one or more inflation chambers positioned
(Continued)

in the digit cavity. The body proximal end includes an upper portion, a lower portion, and two laterally spaced-apart side portions. At least one side portion is distally recessed as compared to the upper and lower portions to accommodate an interdigital fold. At least one flexible bladder lines the digit cavity, each flexible bladder defining at least one wall of one of the one or more inflation chambers.

20 Claims, 33 Drawing Sheets

Related U.S. Application Data

(60) Provisional application No. 62/649,693, filed on Mar. 29, 2018.

(58) Field of Classification Search
USPC .......................................... 606/201, 202, 203
See application file for complete search history.

(56) References Cited

U.S. PATENT DOCUMENTS

| | | | |
|---|---|---|---|
| 4,706,658 A | | 11/1987 | Cronin |
| 4,773,419 A | * | 9/1988 | Tountas ............... A61B 17/135 |
| | | | 600/499 |
| 9,414,653 B1 | | 8/2016 | Morton |
| 2009/0100868 A1 | | 4/2009 | Cai |
| 2009/0209891 A1 | | 8/2009 | Gavriely et al. |

FOREIGN PATENT DOCUMENTS

| | | |
|---|---|---|
| GB | 2255019 A | 10/1992 |
| GB | 2344524 A | 6/2000 |
| WO | 02091929 A1 | 11/2002 |

OTHER PUBLICATIONS

Hennessey et al., Poster, Automated Ring Removal Centre (ARRC), Department of Mechanical Engineering, Group 16, Dalhousie University, dated Mar. 30, 2017.

* cited by examiner

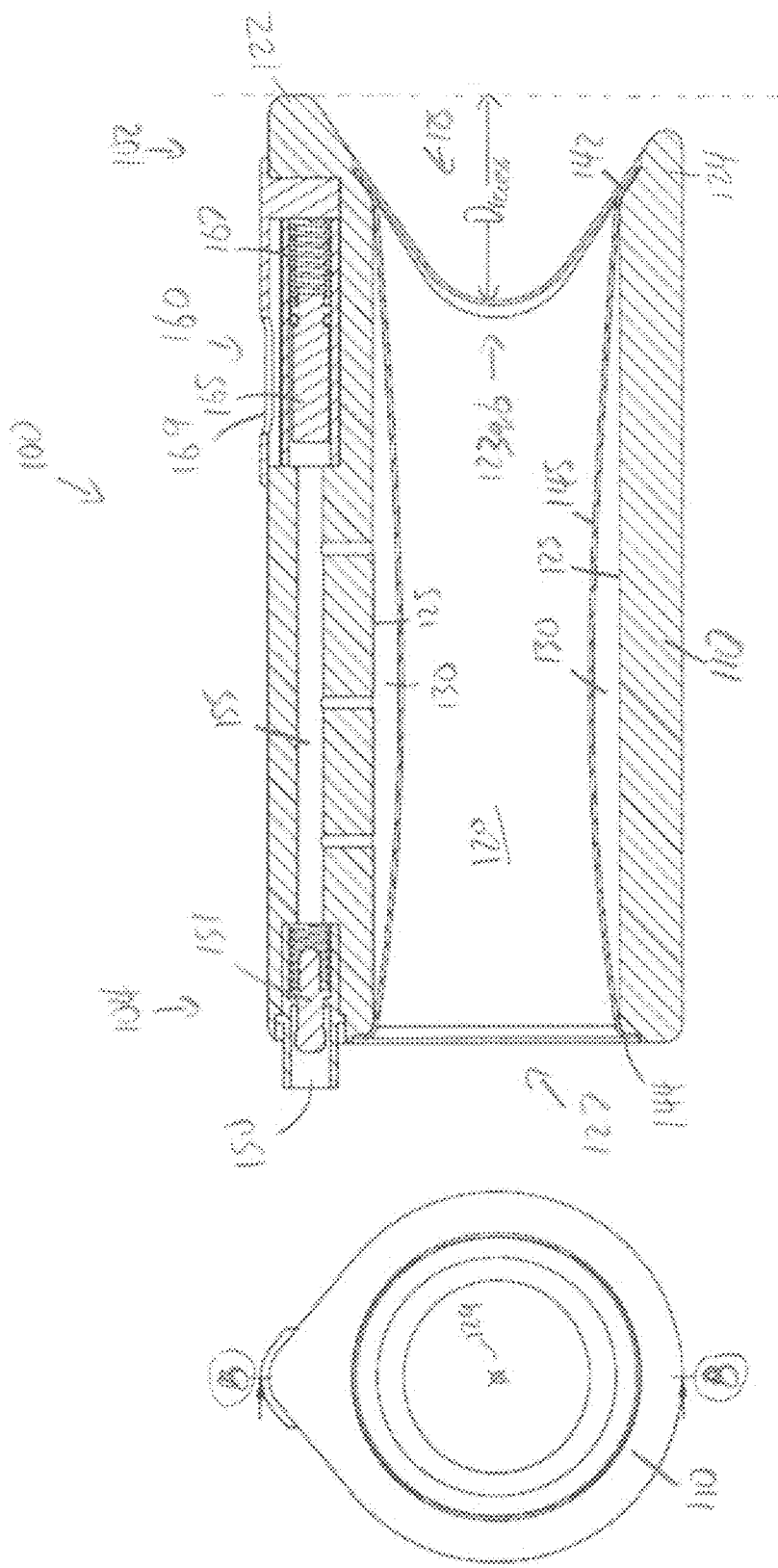

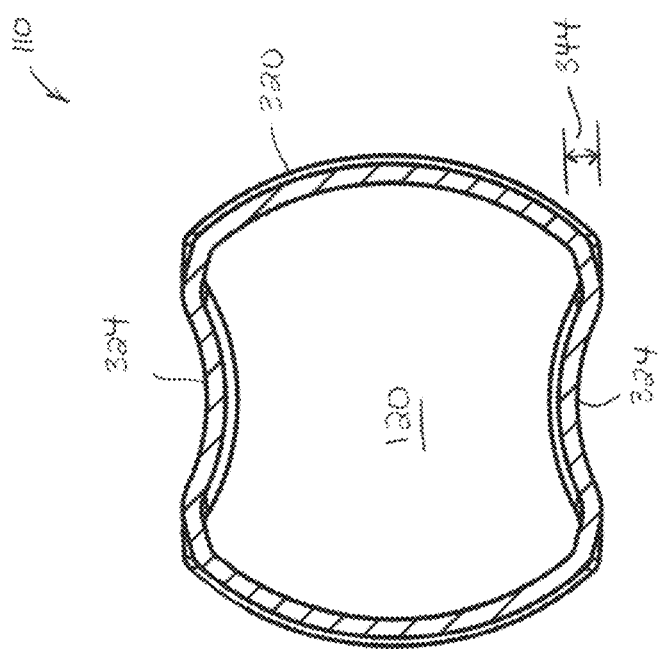

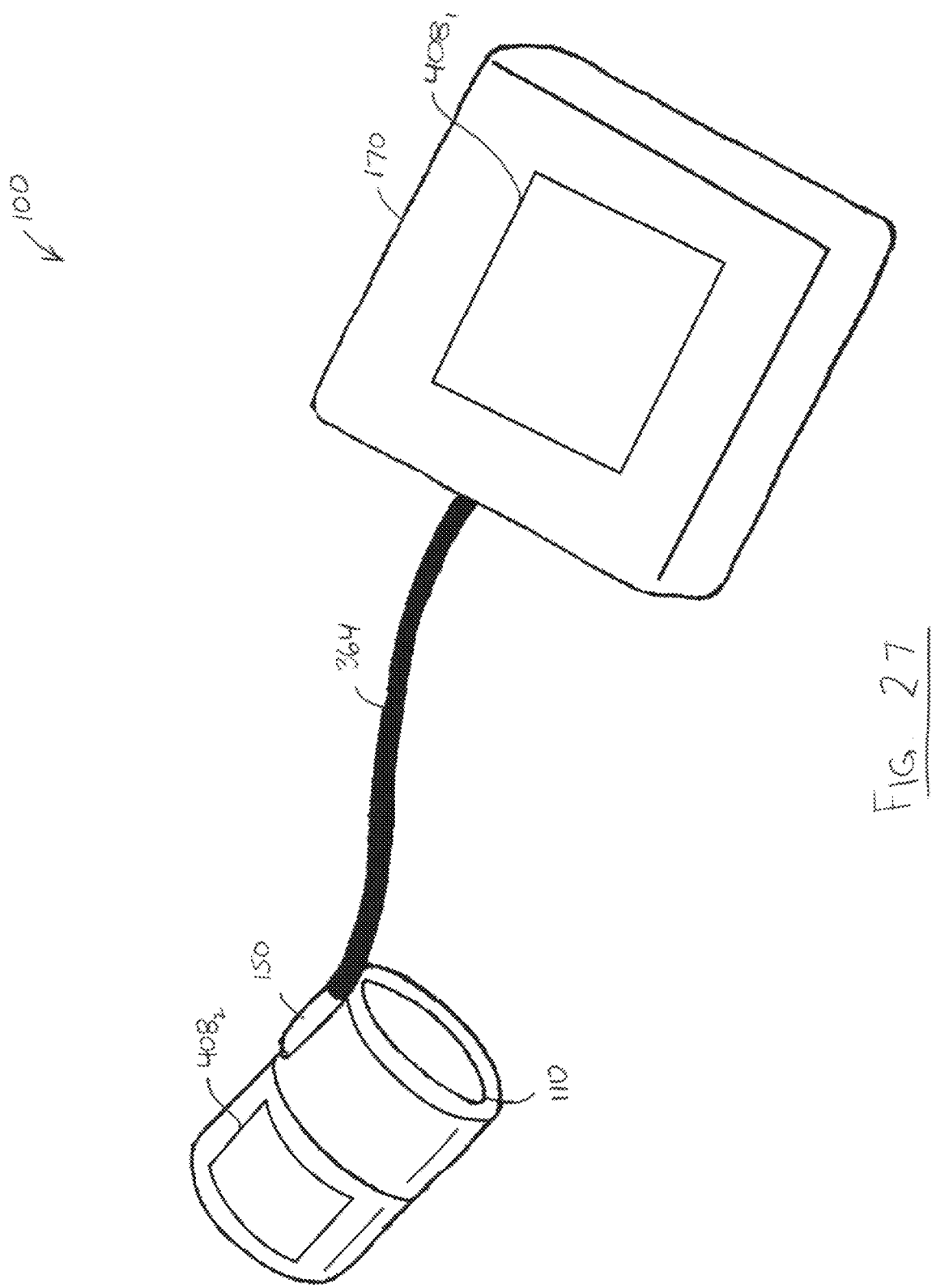

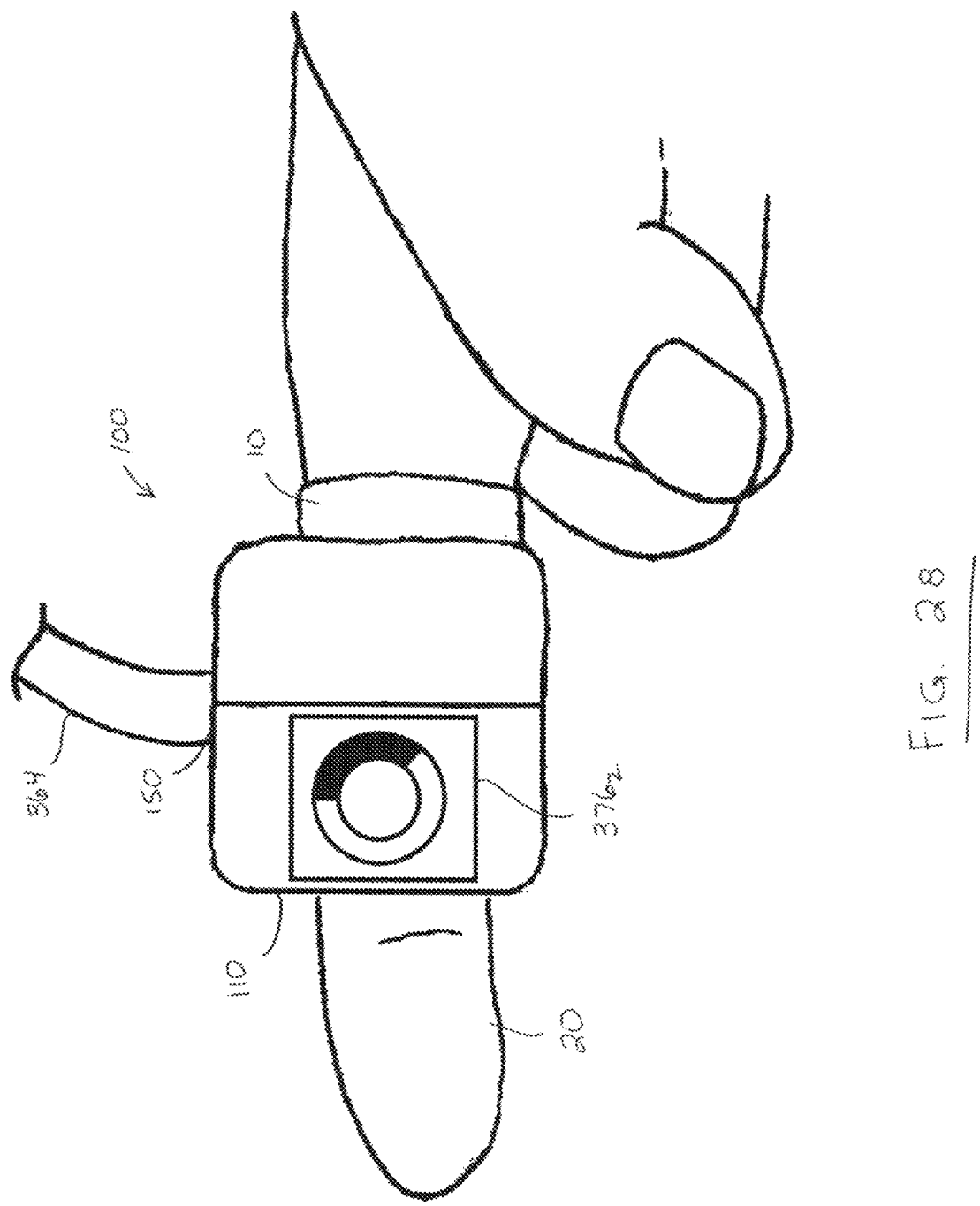

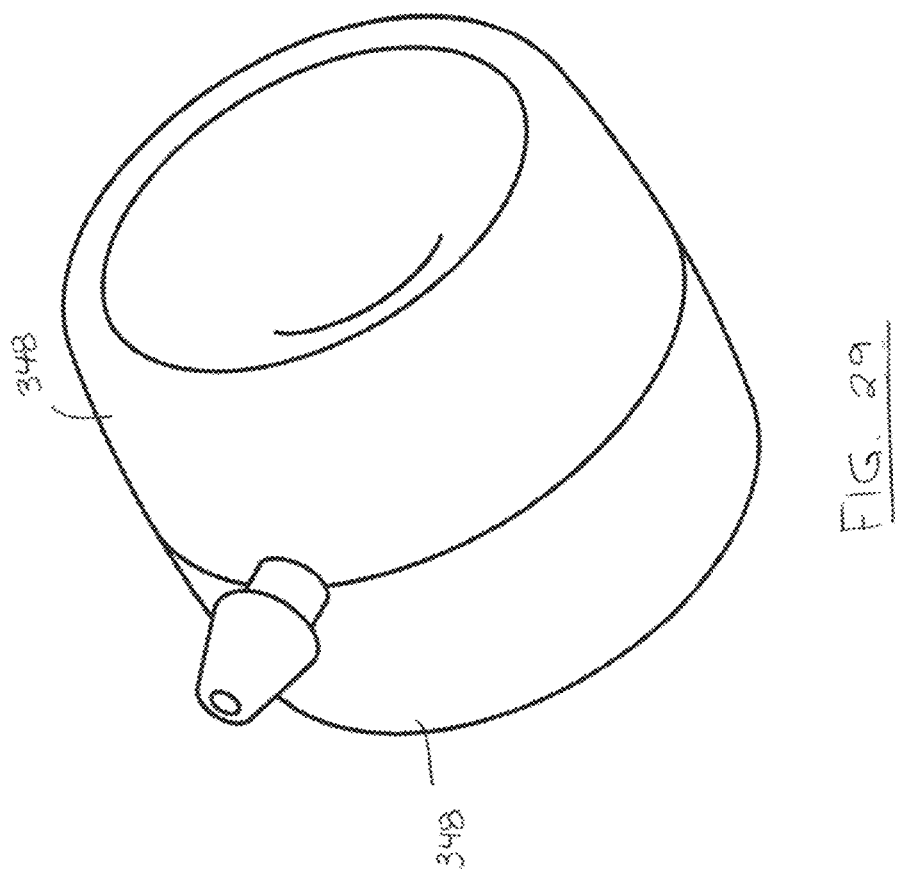

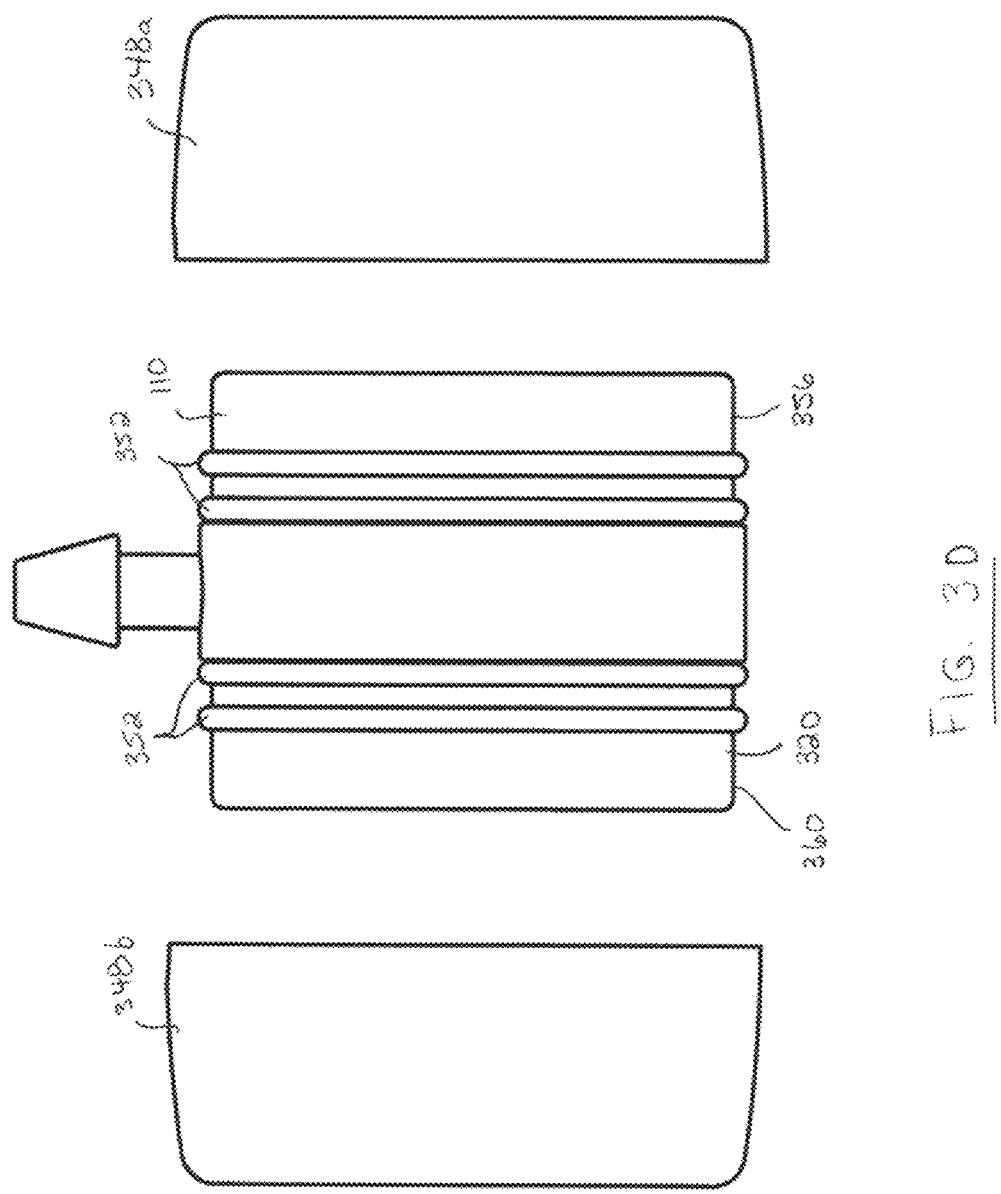

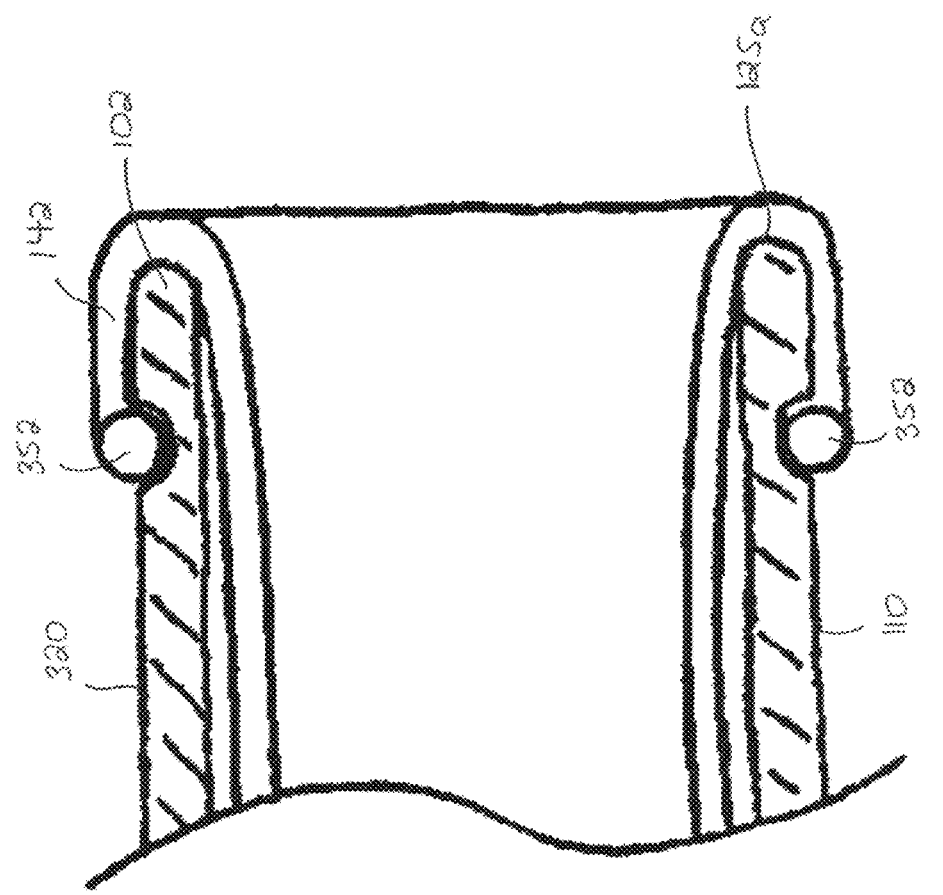

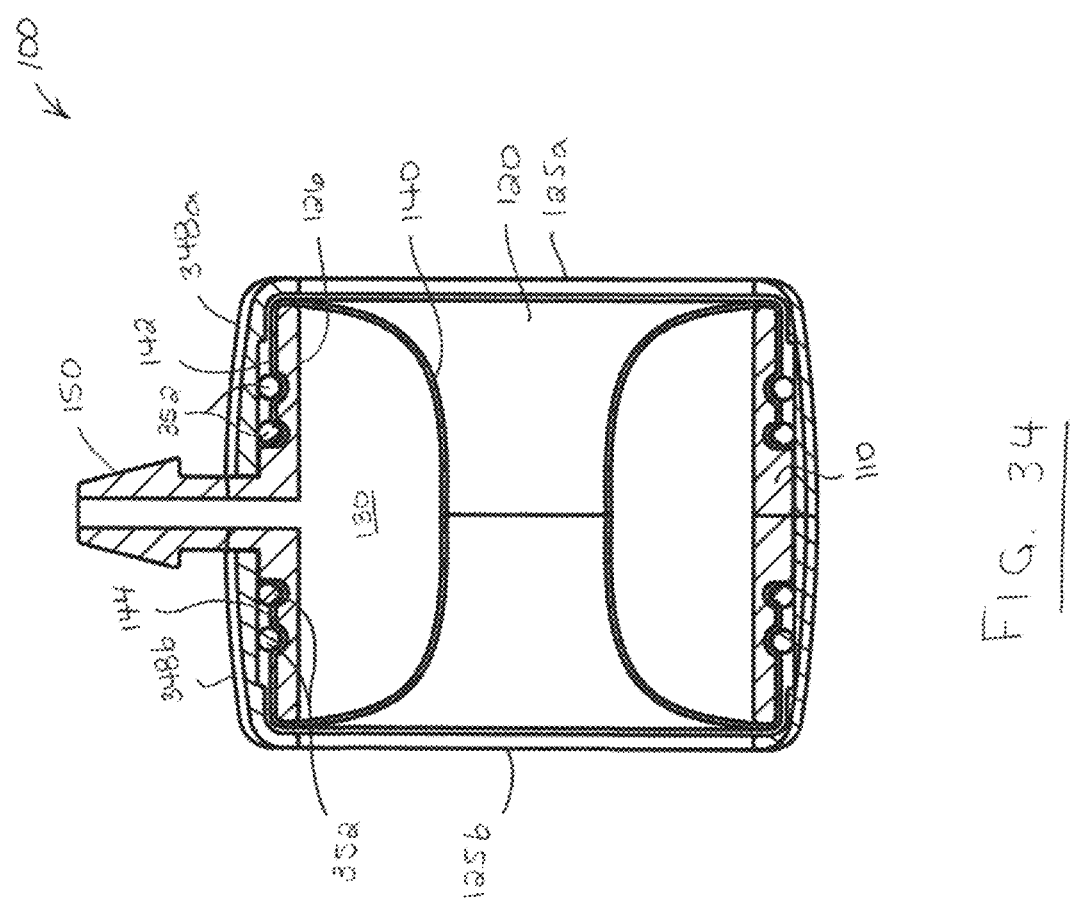

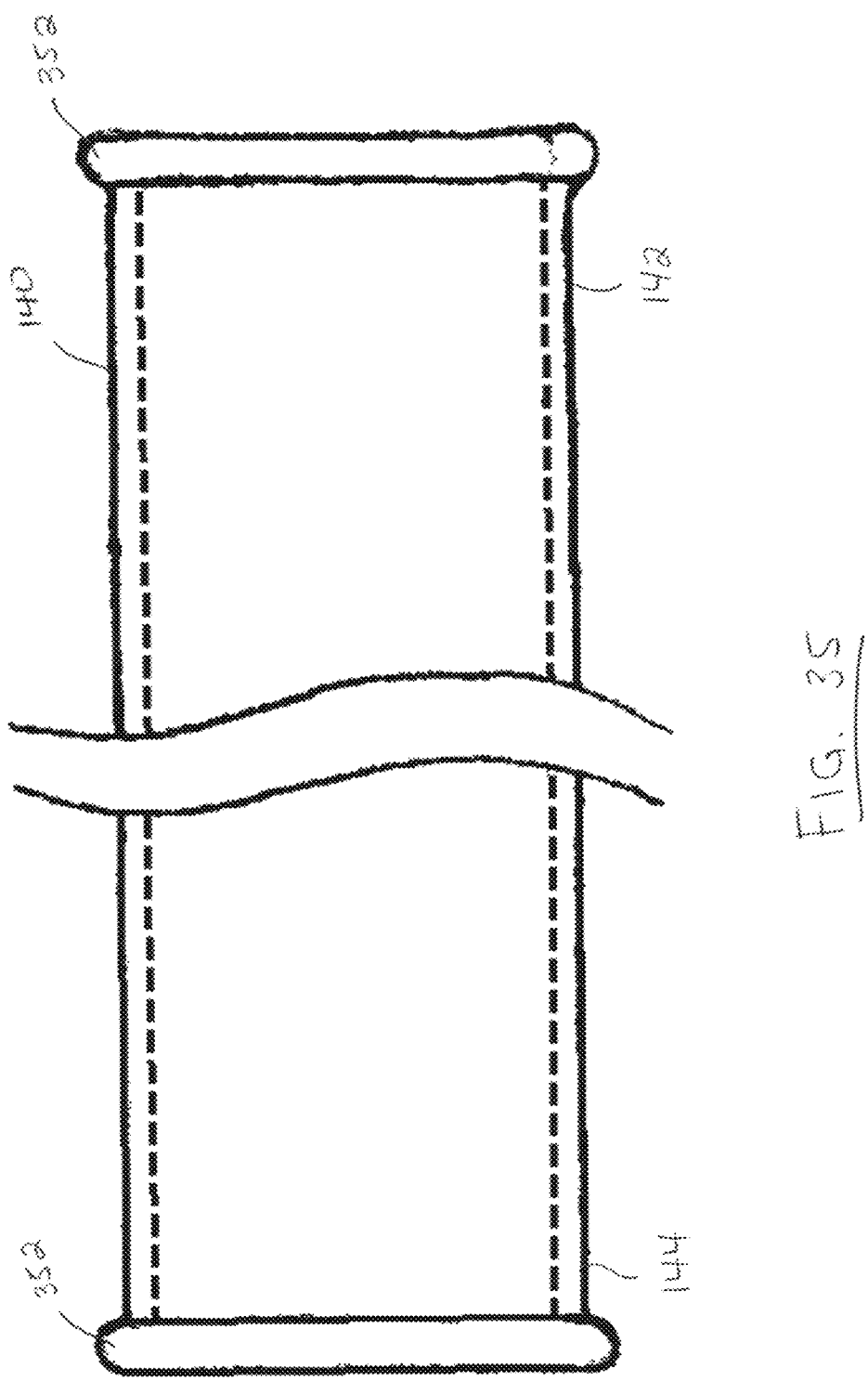

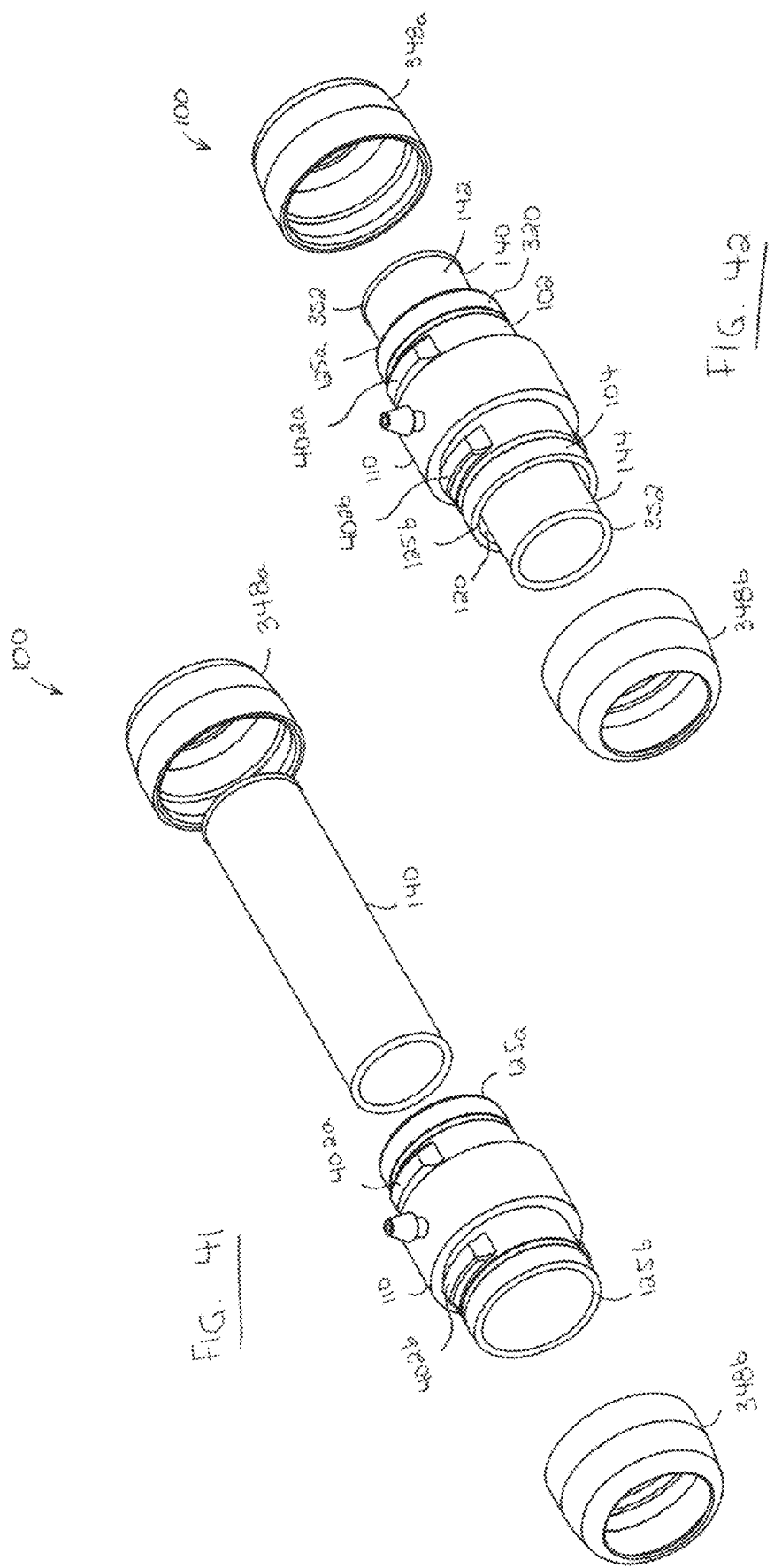

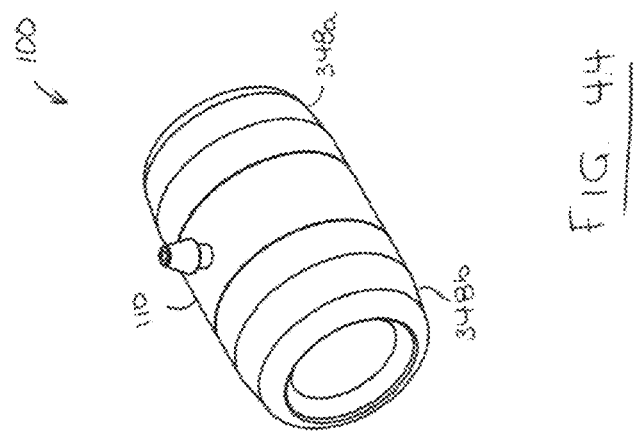
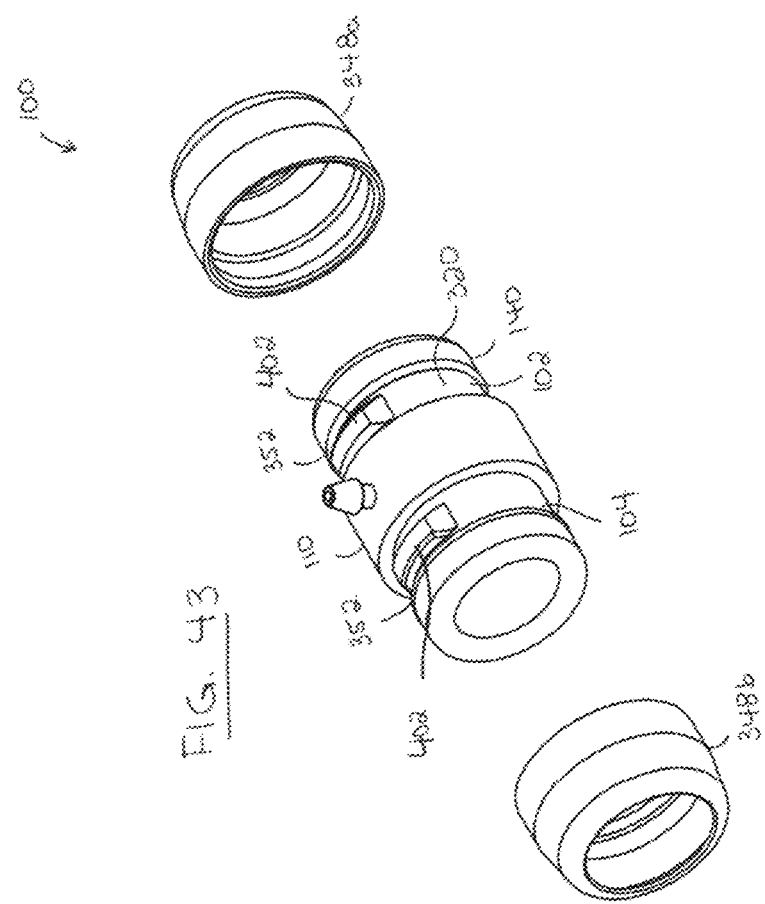

DEVICES AND METHODS FOR COMPRESSING A DIGIT TO FACILITATE REMOVAL OF A RING

FIELD

This disclosure relates generally devices and methods for removing rings or other hand/foot jewelry from a digit (i.e. a digit, thumb, or toe), and more specifically to devices and methods that employ a rigid outer body in which a digit may be inserted, and an inflatable bladder to selectively apply pressure to surface of the inserted digit to promote its compression.

INTRODUCTION

Removing hand/foot jewelry is commonplace in hospital emergency rooms around the world. Rings must be removed from the digits of patients in many, if not most cases where there is swelling of the digit, and/or swelling of the associated hand/foot or arm/leg. In cases where rings cannot be removed easily, the process of removal may be time-consuming, and in some cases may risk the health of the patient.

In the event that a ring is not easily removable from a patient's swollen digit, there are two widely accepted methods for removal of the ring: the 'ring cutter method' and the 'string method'. In the ring cutter method, the ring is cut using e.g. a small rotary saw, and then mechanically deformed to remove it from the digit. In the string method, string or an elastic constrictive material (e.g. a penrose drain) is wrapped tightly around a swollen digit to compress the digit, in an effort to decrease the swelling sufficiently so that the ring can be removed by sliding the ring towards and ultimately past the distal end of the digit.

SUMMARY

The following introduction is provided to introduce the reader to the more detailed discussion to follow. The introduction is not intended to limit or define any claimed or as yet unclaimed invention. One or more inventions may reside in any combination or sub-combination of the elements or process steps disclosed in any part of this document including its claims and figures.

In accordance with one aspect of this disclosure, a compression device for freeing a ring trapped or 'stuck' on a digit includes a rigid outer body or housing, a digit cavity in which a digit on which a ring is stuck may be positioned, and an inflation chamber positioned in the digit cavity. When a swollen digit is positioned in the cavity, the inflation chamber may be inflated to apply and maintain pressure to the exterior of the digit, promoting compression of the digit by forcing endemic fluid from the digit into the hand/foot and surrounding tissue. Once the volume and/or the maximum diameter of the digit has been reduced, the digit may be removed from the device and the ring can be removed by sliding the ring towards and ultimately past the distal end of the digit.

An advantage of this design is that the device may be positioned around a digit in a relatively simple manner, which may reduce the time required to begin compressing the digit once a need or desire to do so is identified.

Another advantage of this design is that the device may allow a relatively uniform pressure to be applied to the entire digit in a relatively simple manner, e.g. without requiring the time and/or skill required to perform the string method. This allows person without medical training (e.g. staff at a jewelry store) to safely and successfully perform the ring removal procedure.

Another advantage is that the device may allow a relatively uniform pressure to be maintained to the digit during its compression. For example, after an initial application of pressure, the volume of the digit may begin to decrease as endemic fluid is forced from the digit. By allowing the volume and/or pressure of fluid within the inflation chamber to be increased as the volume of the inserted digit decreases, a relatively constant pressure may be maintained on the exterior of the digit as its volume decreases. This may increase the amount of endemic fluid the device can remove from the digit in a given time period. Consequently, the apparatus may be used to perform the ring removal procedure quickly.

Preferably, an opening of the digit cavity has at least one side portion that is recessed towards the distal end of the compression device. This recess (also referred to as a hollow) may allow a digit to be positioned deeper into the digit cavity, e.g. by accommodating an interdigital fold (also referred to as a digit web). An advantage of this design is that the inflation chamber may surround more of the digit, which may allow most or preferably substantially all of the digit to be compressed. This may be particularly advantageous for removing rings that are trapped at or near the base of the digit, i.e. a typical location where a ring is worn.

Optionally, two or more inflation chambers may be provided in the digit cavity. An advantage of this design is that it may allow pressure to be selectively and/or sequentially applied to two or more portions of the length of the digit. For example, pressure may be initially applied at the distal end of the digit, and while this initial pressure is maintained, pressure may be subsequently applied to the proximate end of the digit. This may facilitate a positive pressure gradient along the length of the inserted the digit (the gradient increases from the distal end to the proximal end), inhibiting or preventing endemic fluid from flowing towards and/or accumulating in the distal tip of the digit.

In accordance with a broad aspect, there is provided a compression device for freeing a ring trapped on a digit, the compression device comprising: a rigid outer body extending from a body proximal end to a body distal end, the rigid outer body comprising: a digit cavity extending from a cavity opening at the body proximal end towards the body distal end, a fluid inlet, and a fluid flow path fluidly connecting the fluid inlet to one or more inflation chambers positioned in the digit cavity, wherein the body proximal end comprises an upper portion, a lower portion, and two laterally spaced-apart side portions, each side portion connecting the upper portion to the lower portion, at least one side portion being distally recessed as compared to the upper and lower portions to accommodate an interdigital fold; and at least one flexible bladder lining the digit cavity, each flexible bladder defining at least one wall of one of the inflation chambers.

In some embodiments, each side portion is distally recessed as compared to the upper and lower portions.

In some embodiments, the compression device further comprises a fluid pressure gauge rigidly connected to the body and fluidly connected to the fluid flow path.

In some embodiments, the pressure gauge includes a pressure indicator movable in response to fluid pressure within the fluid flow path, and a visual indicium identifying a position of the pressure indicator corresponding to a target pressure.

In some embodiments, the pressure gauge is housed in the rigid outer body.

In some embodiments, the visual indicium is provided on the rigid outer body.

In some embodiments, the rigid outer body defines at least one wall of each of the inflation chambers.

In some embodiments, the digit cavity has a closed distal end.

In some embodiments, the fluid inlet is at the body distal end.

In some embodiments, the fluid inlet comprises a normally-closed valve that is openable by connecting a fluid source.

In some embodiments, the digit cavity has a substantially cylindrical cross-sectional shape.

In some embodiments, the upper and lower portions extend proximally of the two side portions.

In some embodiments, the at least one inflation chamber comprises a first inflation chamber and a second inflation chamber, and the compression device further comprises a flow control valve in the fluid flow path between the first inflation chamber and the second inflation chamber.

In some embodiments, the flow control valve is an orifice valve.

In some embodiments, the rigid outer body is at least one of translucent or transparent.

In some embodiments, at least one of the inflation chambers is at least one of translucent or transparent.

In some embodiments, the compression device further comprises a pressure relief valve in fluid communication with the fluid flow path, and openable to atmosphere in response to a predetermined excessive fluid pressure within the fluid flow path.

In some embodiments, the flexible bladder comprises a tubular sheet extending from a sheet proximal portion to a sheet distal portion, each of the sheet proximal portion and sheet distal portion being sealed fluid tight to the rigid outer body.

It will be appreciated by a person skilled in the art that an apparatus or method disclosed herein may embody any one or more of the features contained herein and that the features may be used in any particular combination or sub-combination.

These and other aspects and features of various embodiments will be described in greater detail below.

BRIEF DESCRIPTION OF THE DRAWINGS

For a better understanding of the described embodiments and to show more clearly how they may be carried into effect, reference will now be made, by way of example, to the accompanying drawings in which:

FIG. 7 is an end view of the proximal end of the compression device of FIG. 4;

FIG. 8 is a section view of the compression device of FIG. 4, taken along line 8-8 in FIG. 7;

FIG. 26 is a cross-sectional view taken along line 26-26 in FIG. 23;

FIG. 27 is a perspective view of a digit compression device connected to a fluid source in accordance with another embodiment;

FIG. 28 is a side view of the digit compression device of FIG. 27 being worn on a digit;

FIG. 29 is a perspective view of the digit compression device of FIG. 27;

FIG. 30 is a side elevation view of a device body with bladder engagement members disengaged, in accordance with an embodiment;

FIG. 33 is a cross-sectional view of a device body with a tubular bladder folded over an exterior surface thereof, in accordance with an embodiment;

FIG. 34 is a cross-sectional view of a digit compression device in accordance with an embodiment;

FIG. 35 is a side elevation view of a tubular bladder with integrated gaskets, in accordance with an embodiment;

FIG. 41 is an exploded view of a digit compression device, in accordance with an embodiment;

FIG. 42 is the digit compression device of FIG. 41, with a bladder inserted;

FIG. 43 is the digit compression device of FIG. 41, with a bladder installed; and FIG. 44 is the digit compression device of FIG. 41, full assembled.

Figure 1:
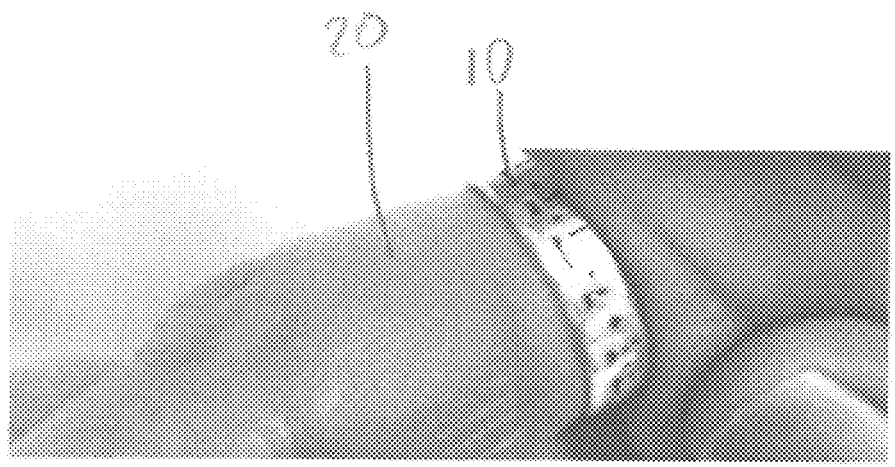
FIG. 1 is an example of a swollen digit with a ring 'stuck' on the digit.

The drawings included herewith are for illustrating various examples of articles, methods, and apparatuses of the teaching of the present specification and are not intended to limit the scope of what is taught in any way.

DESCRIPTION OF EXAMPLE EMBODIMENTS

Various apparatuses, methods and compositions are described below to provide an example of an embodiment of each claimed invention. No embodiment described below limits any claimed invention and any claimed invention may cover apparatuses and methods that differ from those described below. The claimed inventions are not limited to apparatuses, methods and compositions having all of the features of any one apparatus, method or composition described below or to features common to multiple or all of the apparatuses, methods or compositions described below. It is possible that an apparatus, method or composition described below is not an embodiment of any claimed invention. Any invention disclosed in an apparatus, method or composition described below that is not claimed in this document may be the subject matter of another protective instrument, for example, a continuing patent application, and the applicant(s), inventor(s) and/or owner(s) do not intend to abandon, disclaim, or dedicate to the public any such invention by its disclosure in this document.

Furthermore, it will be appreciated that for simplicity and clarity of illustration, where considered appropriate, reference numerals may be repeated among the figures to indicate corresponding or analogous elements. In addition, numerous specific details are set forth in order to provide a thorough understanding of the example embodiments described herein. However, it will be understood by those of ordinary skill in the art that the example embodiments described herein may be practiced without these specific details. In other instances, well-known methods, procedures, and components have not been described in detail so as not to obscure the example embodiments described herein. Also, the description is not to be considered as limiting the scope of the example embodiments described herein.

The terms "an embodiment," "embodiment," "embodiments," "the embodiment," "the embodiments," "one or more embodiments," "some embodiments," and "one embodiment" mean "one or more (but not all) embodiments of the present invention(s)," unless expressly specified otherwise.

The terms "including," "comprising" and variations thereof mean "including but not limited to," unless expressly specified otherwise. A listing of items does not imply that any or all of the items are mutually exclusive, unless expressly specified otherwise. The terms "a," "an" and "the" mean "one or more," unless expressly specified otherwise.

As used herein and in the claims, two or more parts are said to be "coupled", "connected", "attached", "joined", "affixed", or "fastened" where the parts are joined or operate together either directly or indirectly (i.e., through one or more intermediate parts), so long as a link occurs. As used herein and in the claims, two or more parts are said to be "directly coupled", "directly connected", "directly attached", "directly joined", "directly affixed", or "directly fastened" where the parts are connected in physical contact with each other. As used herein, two or more parts are said to be "rigidly coupled", "rigidly connected", "rigidly attached", "rigidly joined", "rigidly affixed", or "rigidly fastened" where the parts are coupled so as to move as one while maintaining a constant orientation relative to each other. None of the terms "coupled", "connected", "attached", "joined", "affixed", and "fastened" distinguish the manner in which two or more parts are joined together.

Further, although method steps may be described (in the disclosure and/or in the claims) in a sequential order, such methods may be configured to work in alternate orders. In other words, any sequence or order of steps that may be described does not necessarily indicate a requirement that the steps be performed in that order. The steps of methods described herein may be performed in any order that is practical. Further, some steps may be performed simultaneously.

As used herein and in the claims, a first element is said to be 'communicatively coupled to' or 'communicatively connected to' or 'connected in communication with' a second element where the first element is configured to send or receive electronic signals (e.g. data) to or from the second element, and the second element is configured to receive or send the electronic signals from or to the first element. The communication may be wired (e.g. the first and second elements are connected by one or more data cables), or wireless (e.g. at least one of the first and second elements has a wireless transmitter, and at least the other of the first and second elements has a wireless receiver). The electronic signals may be analog or digital. The communication may be one-way or two-way. In some cases, the communication may conform to one or more standard protocols (e.g. SPI, $I^2C$, Bluetooth™ or IEEE™ 802.11).

As used herein and in the claims, a group of elements are said to 'collectively' perform an act where that act is performed by any one of the elements in the group, or performed cooperatively by two or more (or all) elements in the group.

Some elements herein may be identified by a part number, which is composed of a base number followed by an alphabetical or subscript-numerical suffix (e.g. $112a$, or $112_1$). Multiple elements herein may be identified by part numbers that share a base number in common and that differ by their suffixes (e.g. $112_1$, $112_2$, and $112_3$). All elements with a common base number may be referred to collectively or generically using the base number without a suffix (e.g. 112).

FIG. 1 depicts a ring 10 that is 'stuck' on a swollen digit 20, in that it cannot be removed by pulling or otherwise mechanically urging the ring towards the distal end of the digit without damaging the digit and/or causing significant pain or discomfort. In the event that a ring is not easily removable from a swollen digit or thumb, there are two widely used methods for removal of the ring: the 'ring cutter method' and the 'string method'.

Figure 2:
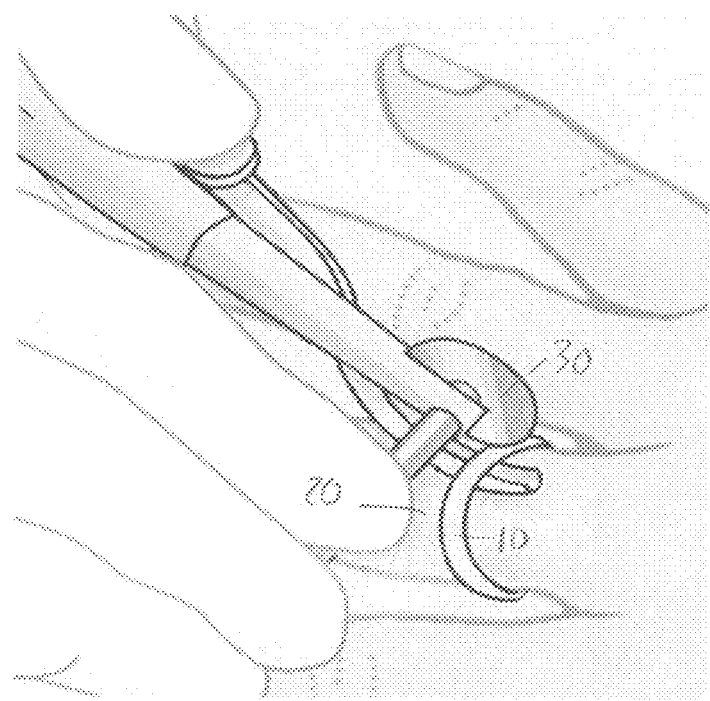
FIG. 2 is an illustration of a ring being removed from a swollen digit by cutting the ring.

In the ring cutter method, a ring 10 is cut using e.g. a small rotary saw (e.g. saw 30 depicted in FIG. 2), and then mechanically deformed to remove it from the digit. While this method may be effective in many cases, it may be difficult or impractical to employ on certain rings (e.g. those made of particularly hard materials such as Tungsten) or if the ring, digit, and/or hand/foot geometry makes it difficult or impractical to position a cutting blade to cut the ring without also cutting or otherwise damaging the surrounding tissue. This method also results in damage to the ring.

Figure 3:
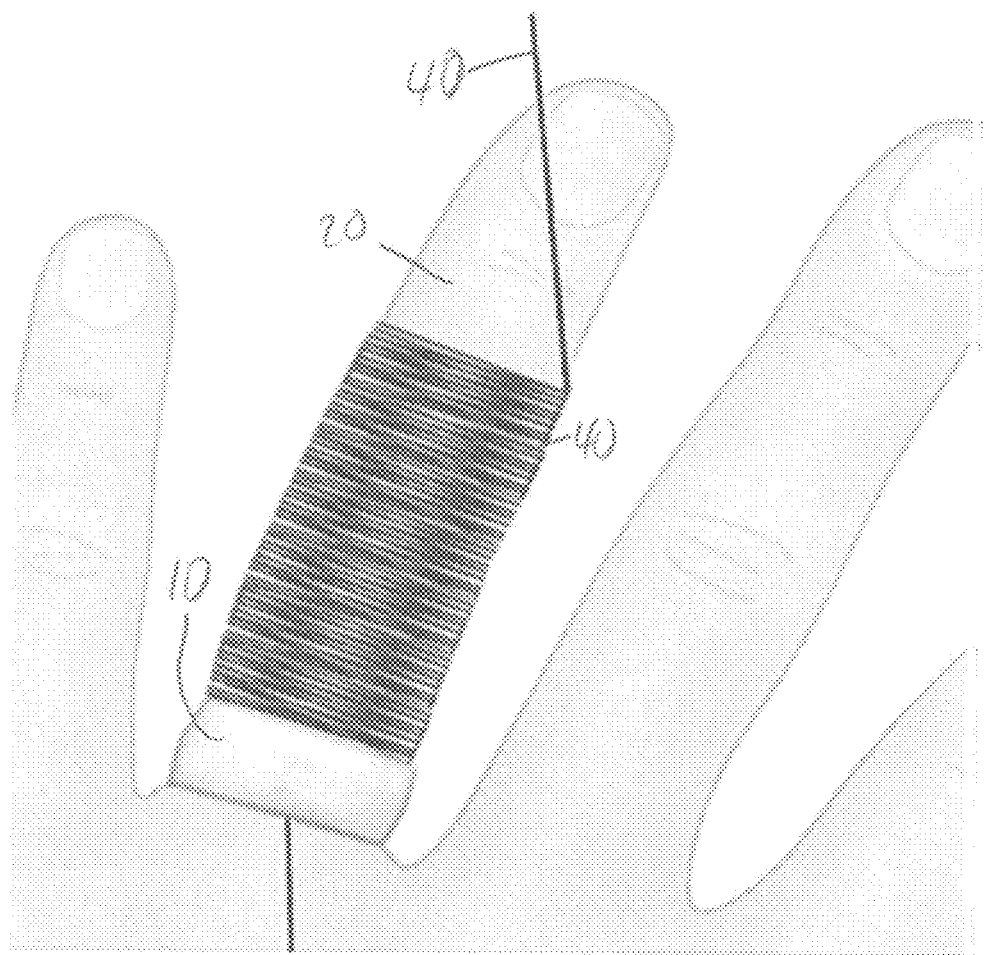
FIG. 3 is an illustration of a ring being removed by using string to compress the digit.

In the string method, string 40 is wrapped tightly around a swollen digit 20 to compress the digit (e.g. as depicted in FIG. 3), in an effort to decrease the swelling sufficiently so that the ring 10 can be removed by sliding the ring towards and ultimately past the distal end of the digit. While this method may be effective in many cases, it may require significant skill and/or dexterity to effectively wrap the string. It may also require a significant amount of time to properly wrap the string, which may be problematic in cases where time is of the essence.

Figure 4:
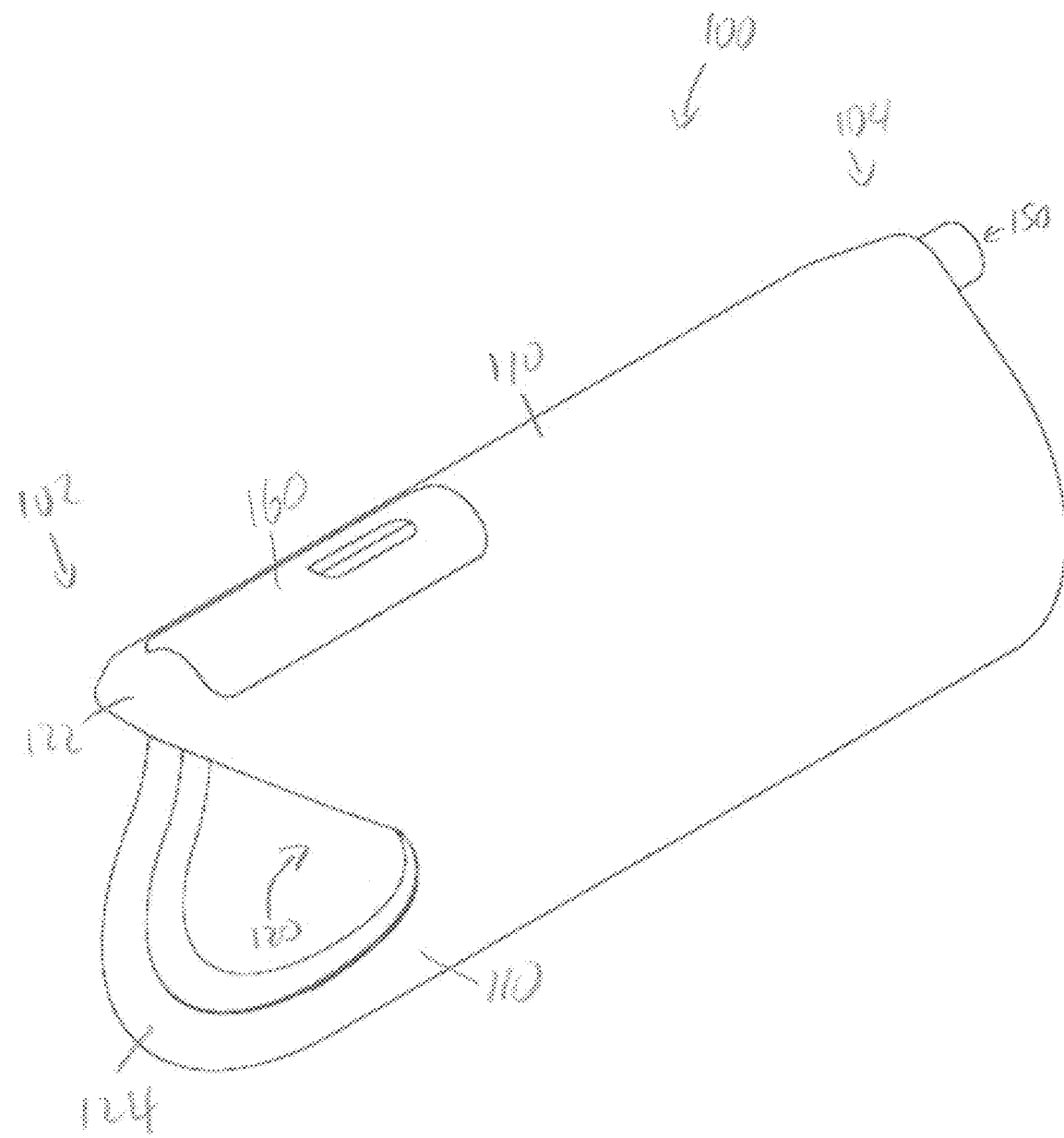
FIG. 4 is a perspective view of a compression device in accordance with one embodiment.

FIG. 4 shows a compression device, referred to generally as 100, for freeing a ring trapped or 'stuck' on a digit or thumb. Compression device 100 includes a rigid outer body 110 (which may also be referred to as a rigid housing, or rigid body), a digit cavity 120 in which a digit on which a ring is stuck may be positioned, and an inflation chamber 130 positioned in the digit cavity. When a swollen digit is positioned in the cavity, the inflation chamber may be inflated to apply and maintain pressure to the exterior of the digit, promoting compression of the digit by forcing endemic fluid from the digit into the hand and surrounding tissue.

Referring now to FIGS. 4 to 8, the body 110 of the compression device 100 has a body proximal end 102 and a body distal end 104. An opening 125 of the digit cavity 120 is provided at the body proximal end 102. When a digit is positioned in the digit cavity, the body proximal end 102 overlies a proximal end of the digit, and the body distal end 104 of the body is positioned at or near a distal end of the inserted digit.

Figure 22:
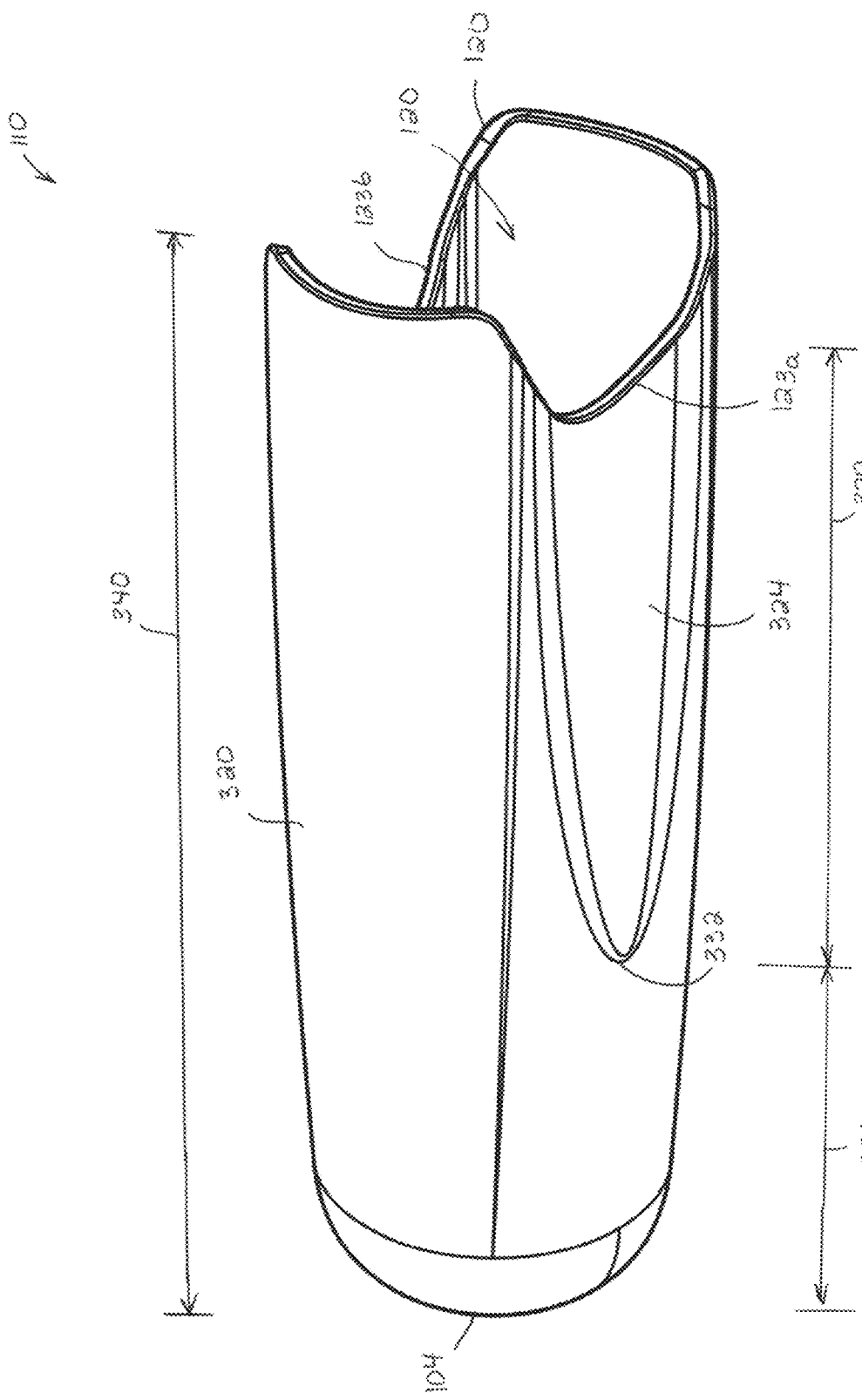
FIG. 22 is a perspective view of a device body in accordance with another embodiment.
Figure 23:
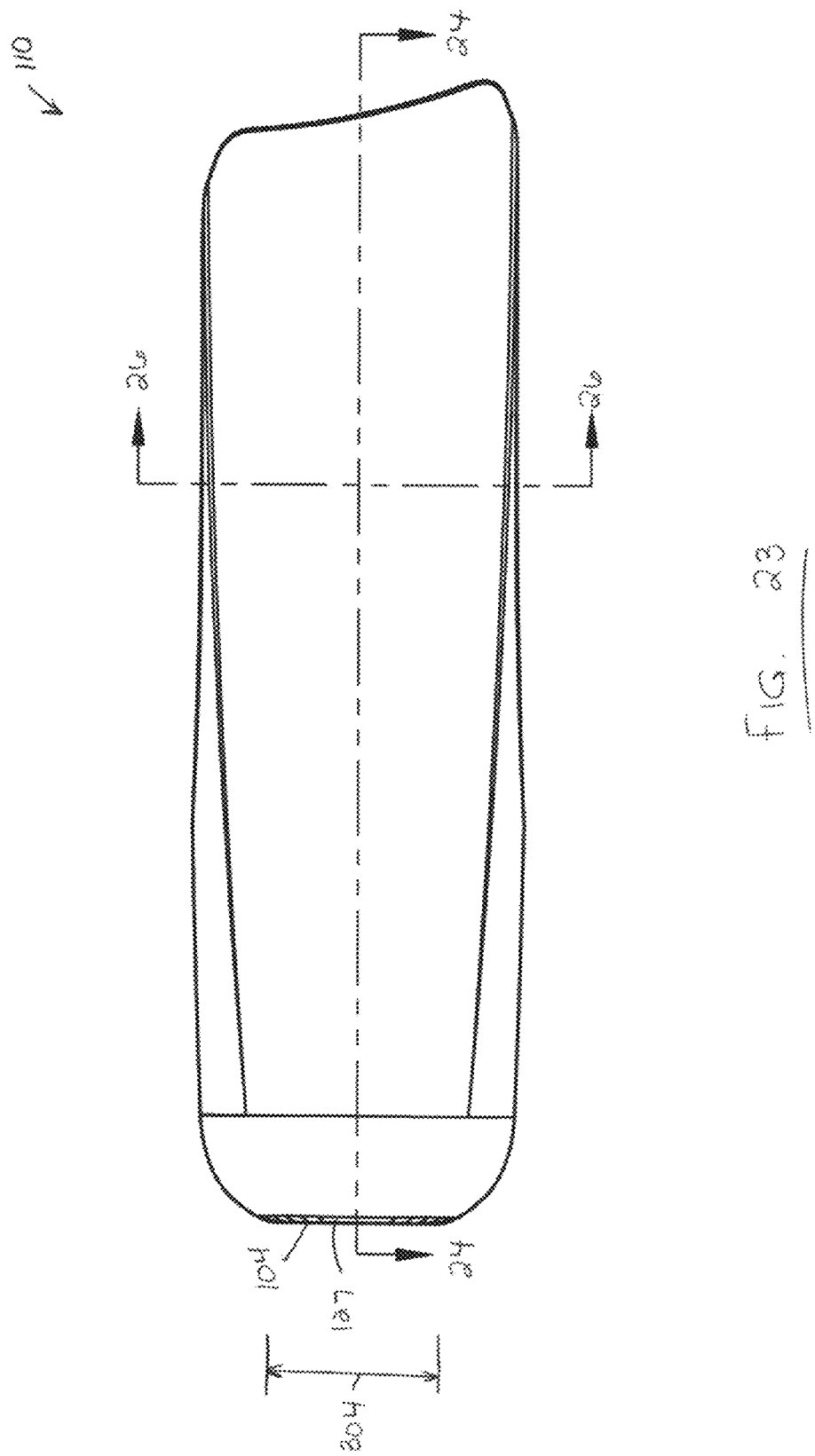
FIG. 23 is a top plan view of the device body of FIG. 22.
Figure 24:
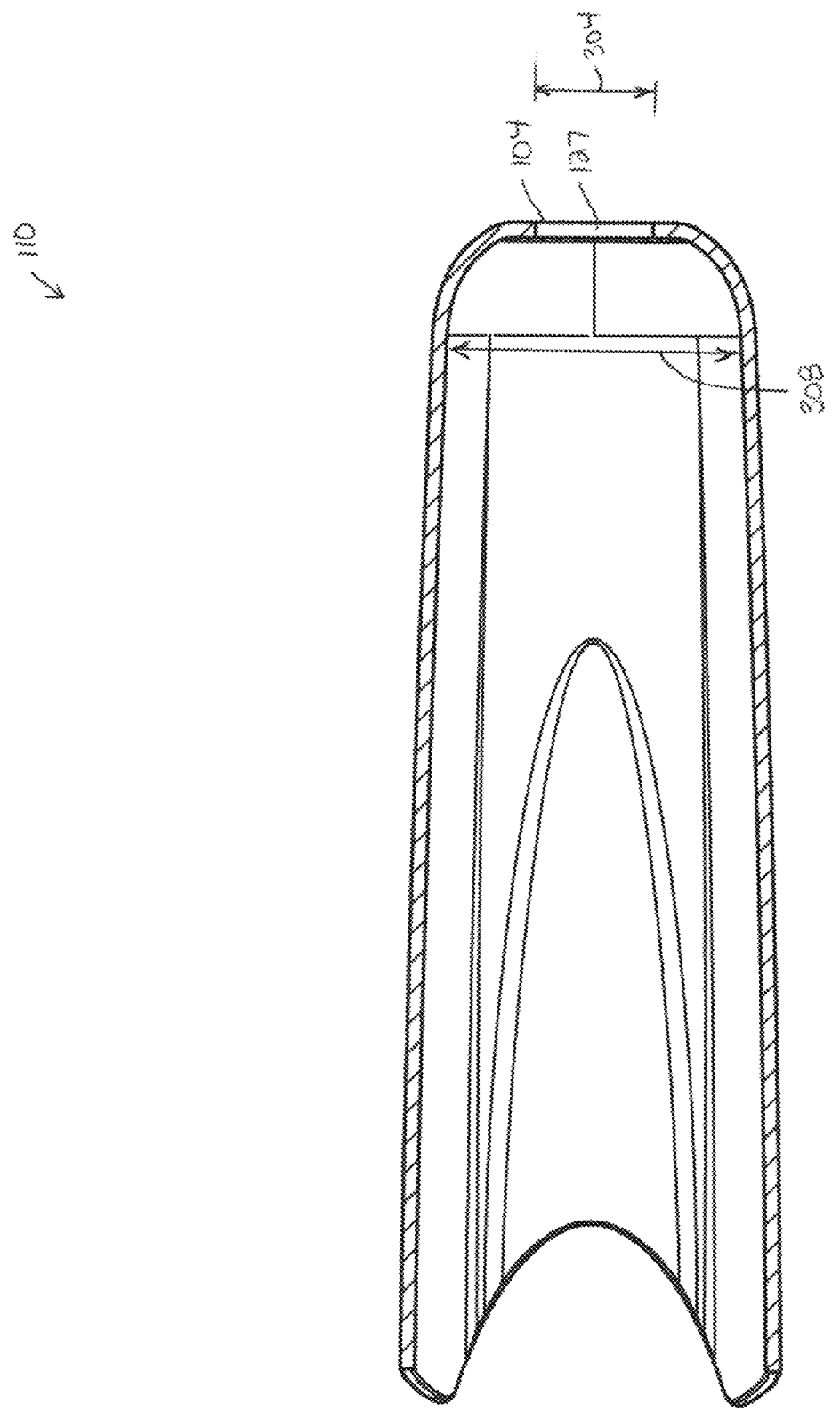
FIG. 24 is a cross-sectional view taken along line 24-24 in FIG. 23.

In the illustrated example, an auxiliary opening 127 is provided at the body distal end 104 to provide access to the digit cavity 120. For example, when a digit is inserted into the opening 125 at the body proximal end 102, fluid (e.g. air) may be evacuated from the digit cavity 120 via the auxiliary opening 127. Alternatively, the body distal end 104 may be substantially or completely closed, such that the digit cavity 120 cannot be accessed from the body distal end 104. FIGS. 22-24 show an embodiment of body 110 in which body distal end 104 is partially closed. As shown, body distal end 104 may include a an auxiliary opening 127 with a width (e.g. diameter) 304. Width 304 may be less than 60% of digit cavity width 308 at body distal end 104 (e.g. between 5% and 60% of digit cavity width 308).

In the illustrated example, the digit cavity opening 125 includes an upper portion 122 and a lower portion 124. A first side portion 123a and a second side portion 123b each connect the upper portion 122 to the lower portion 124. Preferably, at least one of the side portions 123a, 123b is distally recessed relative to the upper portion 122 and the lower portion 124. Providing a recessed side portion 123 may allow the compression device 100 to be positioned over most or substantially all of a digit, as the recessed side portion may accommodate e.g. an interdigital fold between adjacent digits.

Figure 25:
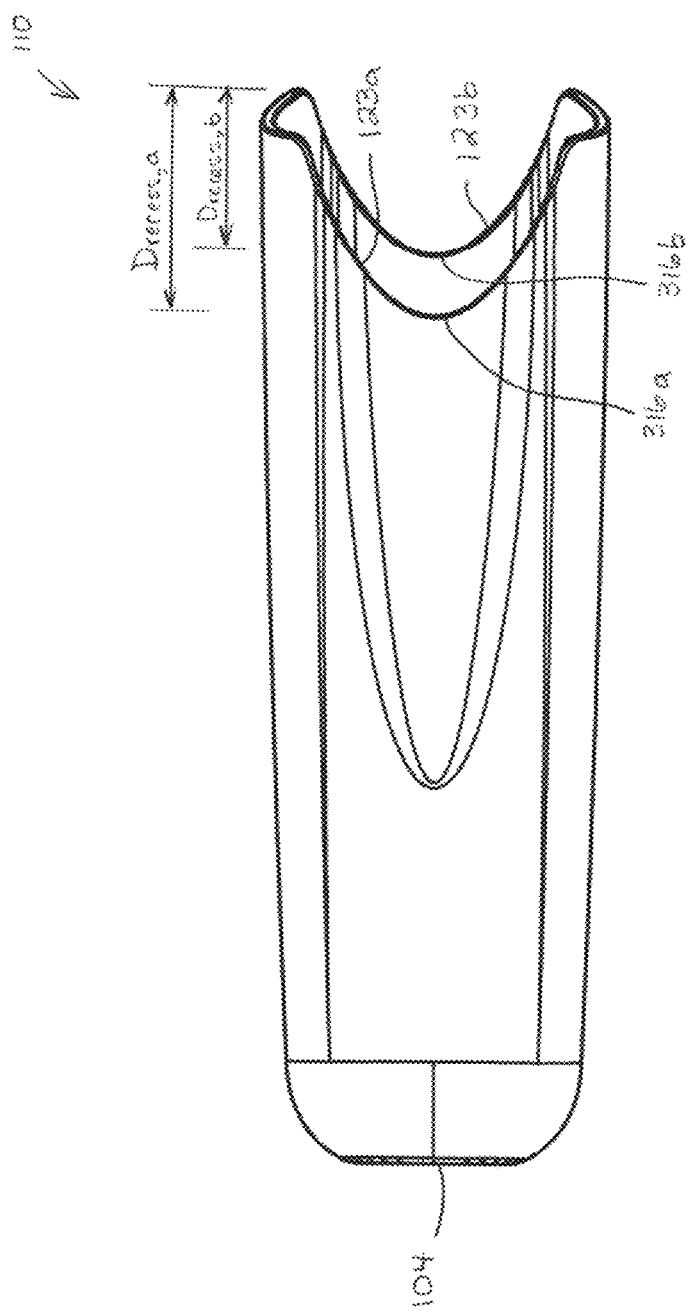
FIG. 25 is a side elevation view of the device body of FIG. 22.

In the illustrated example, both side portions 123a, 123b are distally recessed by the same distance $D_{recess}$, although it will be appreciated that the side portions 123a, 123b may be recessed by different distances. For example, FIG. 25 shows an embodiment in which side portion 123a is more distally recessed than side portion 123b. That is, recess 312a of side portion 123a has a recess distal end 316a (e.g. a recess apex) closer to body distal end 104 than is recess distal end 316b of recess 312b. An advantage of this design is that it can allow a digit to be positioned deeper in the digit cavity. For example, the interdigital folds on either side of a person's fingers are not typically aligned—instead, one interdigital fold is typically positioned proximally of the other. The differing recess distance $D_{recess}$ of recesses 312a and 312b may help body 110 better conform to this anatomical relationship.

Recess distances $D_{recess}$ may be any distance suitable to at least partially accommodate an interdigital fold. In some embodiments, the recess distance $D_{recess}$ may be between 5 mm and 40 mm. In embodiments where the recess distance $D_{recess}$ differs between recesses 312a and 312b, the difference (e.g. difference in distance between each recess distal end 316 and body distal end 104) may be between 2 mm and 25 mm.

In some embodiments, only one side portion may be distally recessed.

Figure 5:
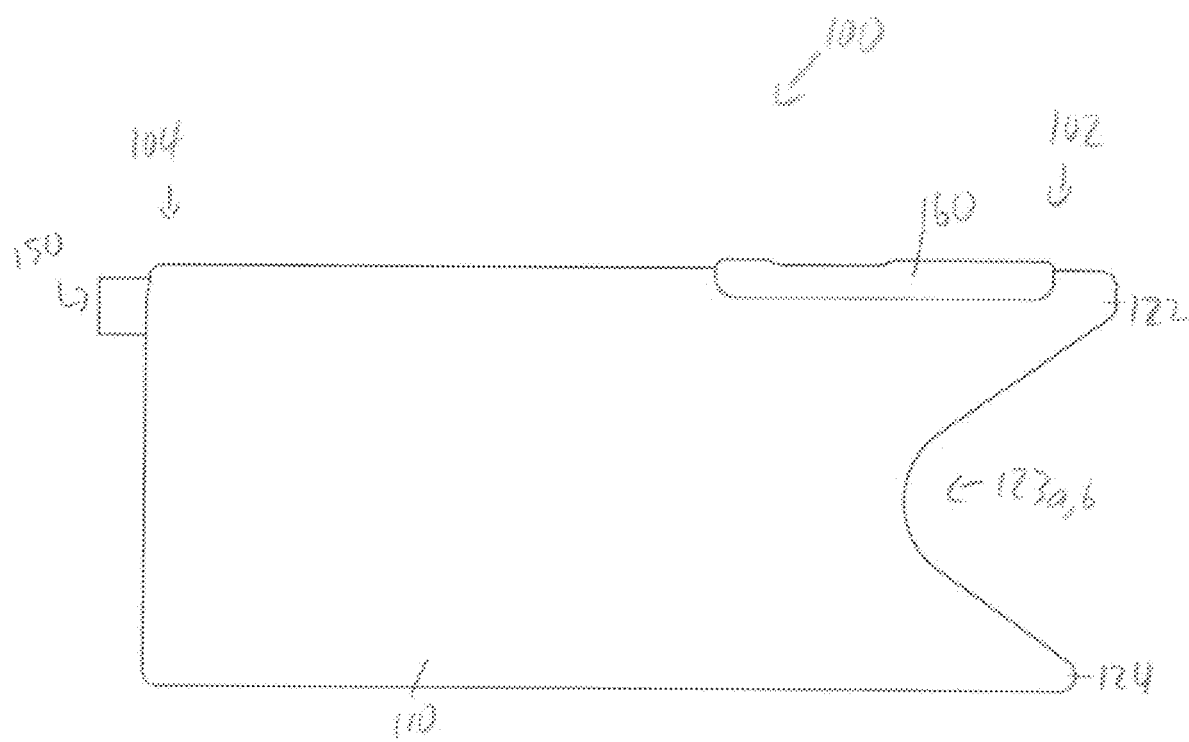
FIG. 5 is a side view of the compression device of FIG. 4.
Figure 6:
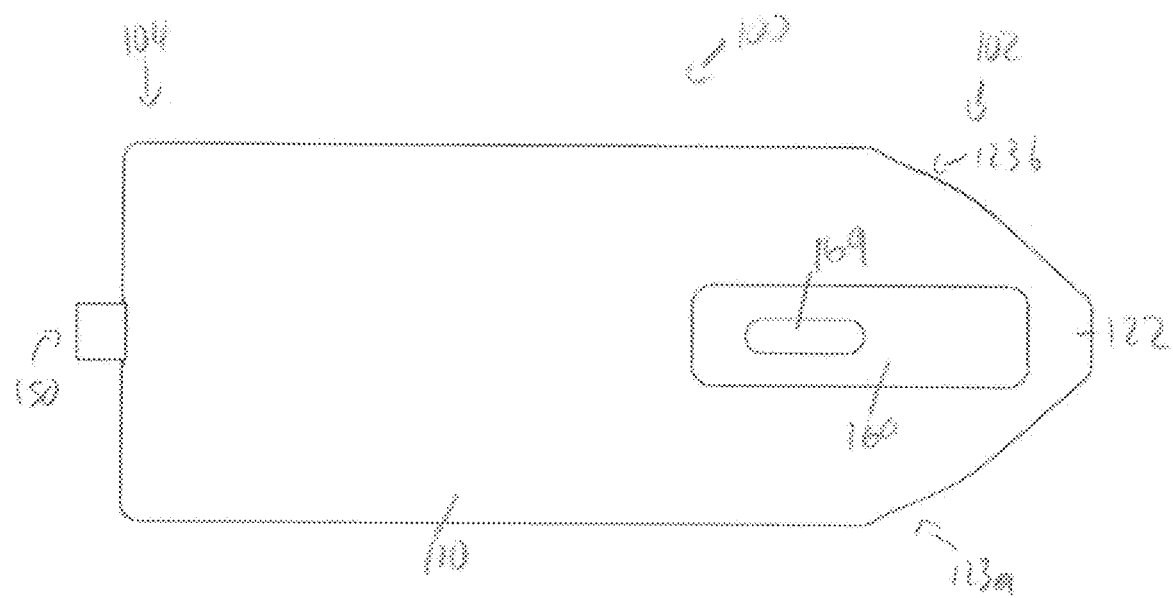
FIG. 6 is a top view of the compression device of FIG. 4.

Also, in the illustrated example both side portions 123a, 123b have the same profile (e.g. as seen in FIG. 5), although it will be appreciated that they may have different profiles in alternative embodiments.

Referring to FIGS. 22 and 26, in some embodiments body 110 has an exterior surface 320 that includes one or two lateral concavities 324. Each lateral concavity 324 provides some accommodation for a digit adjacent to the digit located inside digit cavity 120. This may make wearing compression device 100 more comfortable. As shown, each lateral concavity 324 may extend from a respective side portion 123 of body proximal end 102. This may provide digit accommodation at the base of the wearer's digit, where the digits connect to the hand/foot. As compared to the distal ends of their digits, the wearer has very little capability to spread the distance between the proximal ends of their digits to accommodate compression device 100.

Lateral concavity 324 may extend the entire length of body 110 or may extend a portion of the length of body 110 as shown. In the illustrated example, lateral concavities 324 have an axial length 328 that is less than the body length. As shown, a distal end 332 of each lateral concavity 324 may be spaced from body distal end 104. For example, lateral concavity distal end 332 may be spaced from body distal end 104 by a distance 336 of 15% or more (e.g. between 15% and 50%) of body length 340.

Each lateral concavity 324 may have any depth 344 suitable to accommodate at least a portion of an adjacent digit. In some embodiments, depth 344 is at least 3 mm (e.g. between 3 mm and 10 mm).

Referring to FIG. 8, an inflation chamber 130 is provided in the digit cavity. In the illustrated example, the inflation chamber is defined by an interior surface 126 of the body 110, and by a flexible bladder 140. In the embodiment illustrated in FIG. 8, bladder 140 comprises a flexible tubular sheet 145, with a distal end portion 144 of the sheet 145 secured at the distal end 104 of the body 110, and a proximal end portion 142 of the sheet 145 secured at the proximal end 102 of the body 110. In this example, the sheet 145 of bladder 140 forms an interior wall 147 of the inflation chamber 130.

The inflation chamber 130 is in fluid communication with a fluid inlet 150 of the compression device 100 via a fluid flow path 155. In this way, fluid introduced to the compression device 100 via the fluid inlet 150 is directed towards the interior of the inflation chamber 130. Since the interior surface 126 of the rigid body 110 is relatively inflexible compared to the flexible sheet 145, as fluid is introduced to the inflation chamber 130, the flexible sheet 145 may be urged inwardly towards a longitudinal axis 129 of the digit cavity 120 whereby the flexible sheet 145 may apply pressure onto a digit situated in digit cavity 120.

In an alternative arrangement (not shown), the bladder 140 may define substantially all of the walls of the inflation chamber, e.g. with one wall of the bladder facing or abutting the interior surface 126 of the rigid body 110, and another wall of the bladder facing the interior of the digit cavity 120. In such an arrangement, as fluid is introduced to the flexible bladder 140, the wall of the bladder facing the interior of the digit cavity 120 may be urged towards the longitudinal axis 129 of the digit cavity 120 (as the wall of the bladder facing or abutting the interior surface 126 of the rigid body 110 may be restrained by the housing interior surface 126).

The flexible bladder 140 may be made from any suitable material, such as silicone, an elastomer, a polyvinyl chloride (PVC) membrane, and the like. Preferably, at least the interior wall 147 of the flexible bladder is a biocompatible material that is not expected to irritate or otherwise react with the skin of an inserted digit. Optionally, the flexible bladder 140 may be made from a translucent or substantially transparent material, such as a translucent or transparent silicone elastomer. Providing a translucent or transparent bladder 140 may facilitate observation of the inserted digit, particularly where the rigid body 110 is made from a translucent or substantially transparent material. As used herein, a material is said to be 'translucent' or 'at least translucent' where at least 25% of incident visible light can pass through the material. As used herein, a material is said to be 'transparent' or 'substantially transparent' where at least 75% of incident visible light can pass through the material.

Optionally, a flow control device (e.g. a valve) may be provided between the fluid inlet 150 and the fluid flow path 155. For example, as shown in FIG. 8, a normally closed check valve 151 may be provided to prevent fluid from exiting the fluid flow path 155 via the fluid inlet 150.

Figure 19:
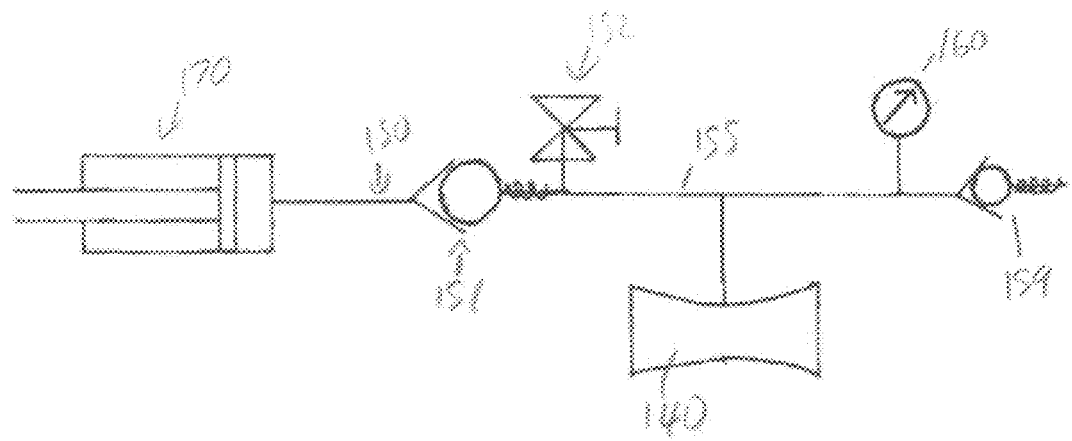
FIG. 19 is a schematic example of a pressure circuit for a compression device.

Additionally, or alternatively, a manually operated valve may be provided between the fluid inlet 150 and the fluid flow path 155. For example, in the schematic pressure circuit example shown in FIG. 19, a manually operated valve 152 is provided between the check valve 151 and the fluid flow path 155.

Optionally, a fluid pressure gauge may be connected to the compression device 100 to provide an indication of fluid pressure within the inflation chamber 130. For example, as shown in FIGS. 4 to 8, a fluid pressure gauge 160 may be provided on the upper end of compression device 100. As shown in FIG. 8, fluid pressure gauge 160 is in fluid communication with fluid flow path 155. In the illustrated example, as the pressure of fluid in the fluid flow path 155 increases, a slider 165 is urged against a compression spring 167. A viewing window 169 allows visual observation of the relative position of the slider 165 (see FIG. 13). It will be appreciated that the pressure gauge may be of any other type suitable for providing the user with an indication of the internal fluid pressure.

Figure 13:
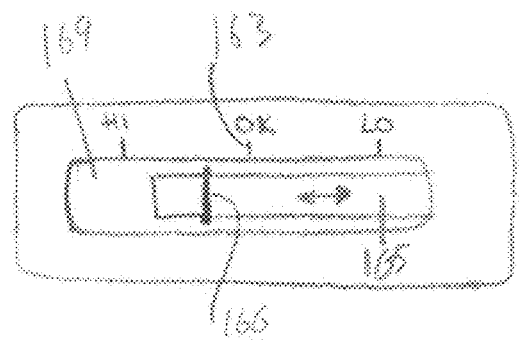
FIG. 13 is a schematic view of a pressure indicator of a pressure gauge.
Figure 14:
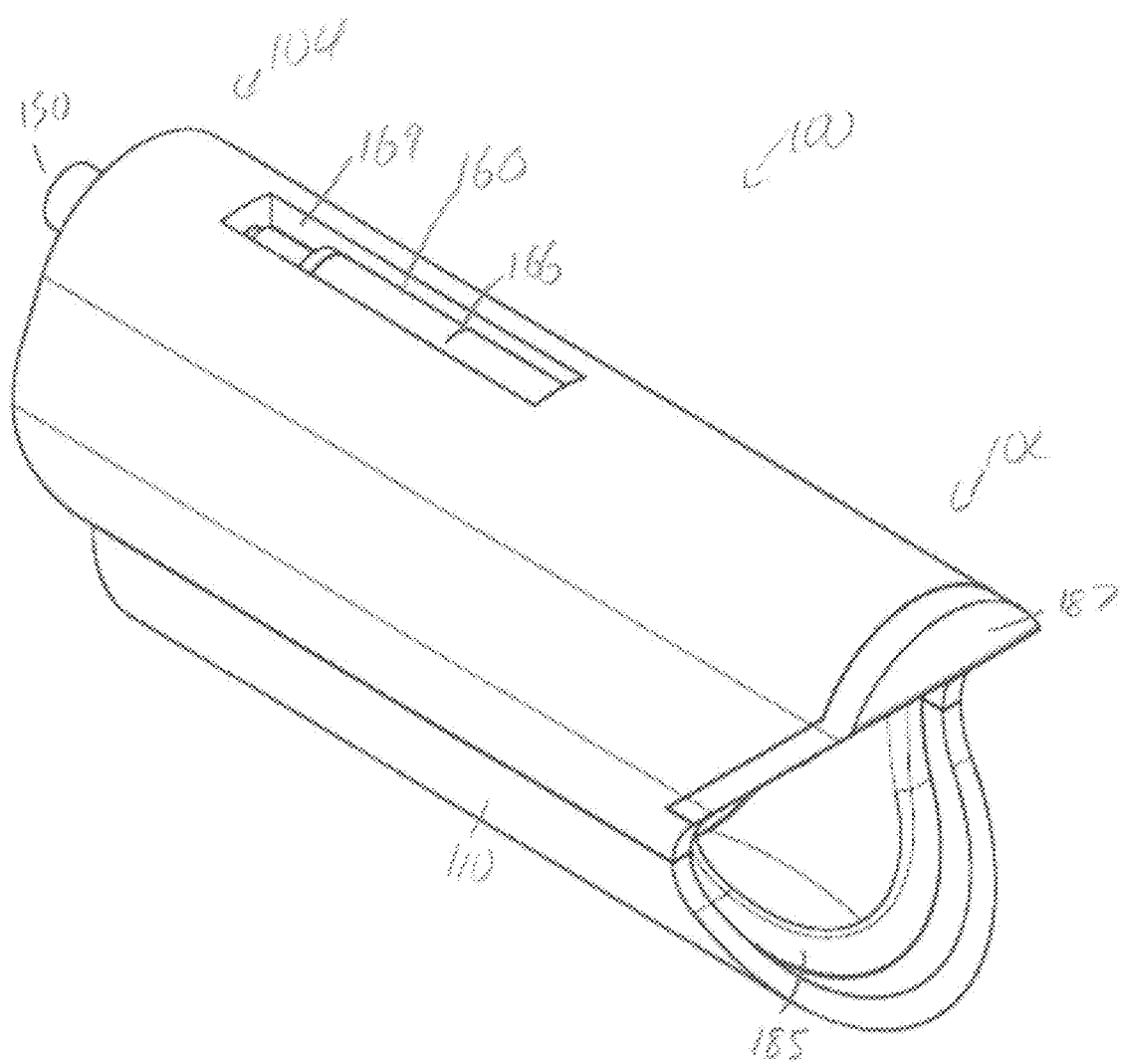
FIG. 14 is a perspective view of a compression device in accordance with another embodiment.

Optionally, the pressure gauge may include a visual indicium of a target pressure range and/or target pressure for the inflation chamber. For example, as illustrated in FIG. 13, the slider 165 has a line 166 or other visual reference mark, and markings 163 such as "HI", "OK", and "LO" are provided adjacent the viewing window 169. It will be appreciated that any suitable visual markings may be alternatively and/or additionally provided. For example, one or more colours may be provided instead of text markings.

Optionally, a pressure relief valve or other safety valve may be provided in fluid communication with the fluid flow path 155 to prevent excessive pressure in the inflation chamber from applying excessive force to an inserted digit and/or from damaging to the compression device. For example, in the schematic pressure circuit example shown in FIG. 19, a relief valve 159 is provided adjacent the fluid pressure gauge 160.

The rigid body 110 may be made from any suitable material, such as metal, plastic, thermoplastic, composite (e.g. carbon fiber) and the like. Optionally, the body 110 may be made from a translucent or substantially transparent material, such as a translucent or transparent plastic or thermoplastic. Providing a translucent or transparent body 110 may facilitate observation of the inflation chamber and/or the inserted digit (e.g. where the flexible bladder is also translucent or transparent). This can allow the operator and the patient to monitor the finger during the procedure.

Use of a compression device 100 to facilitate the removal of a ring trapped on a digit will now be described with reference to FIGS. 9 to 13.

Figure 9:
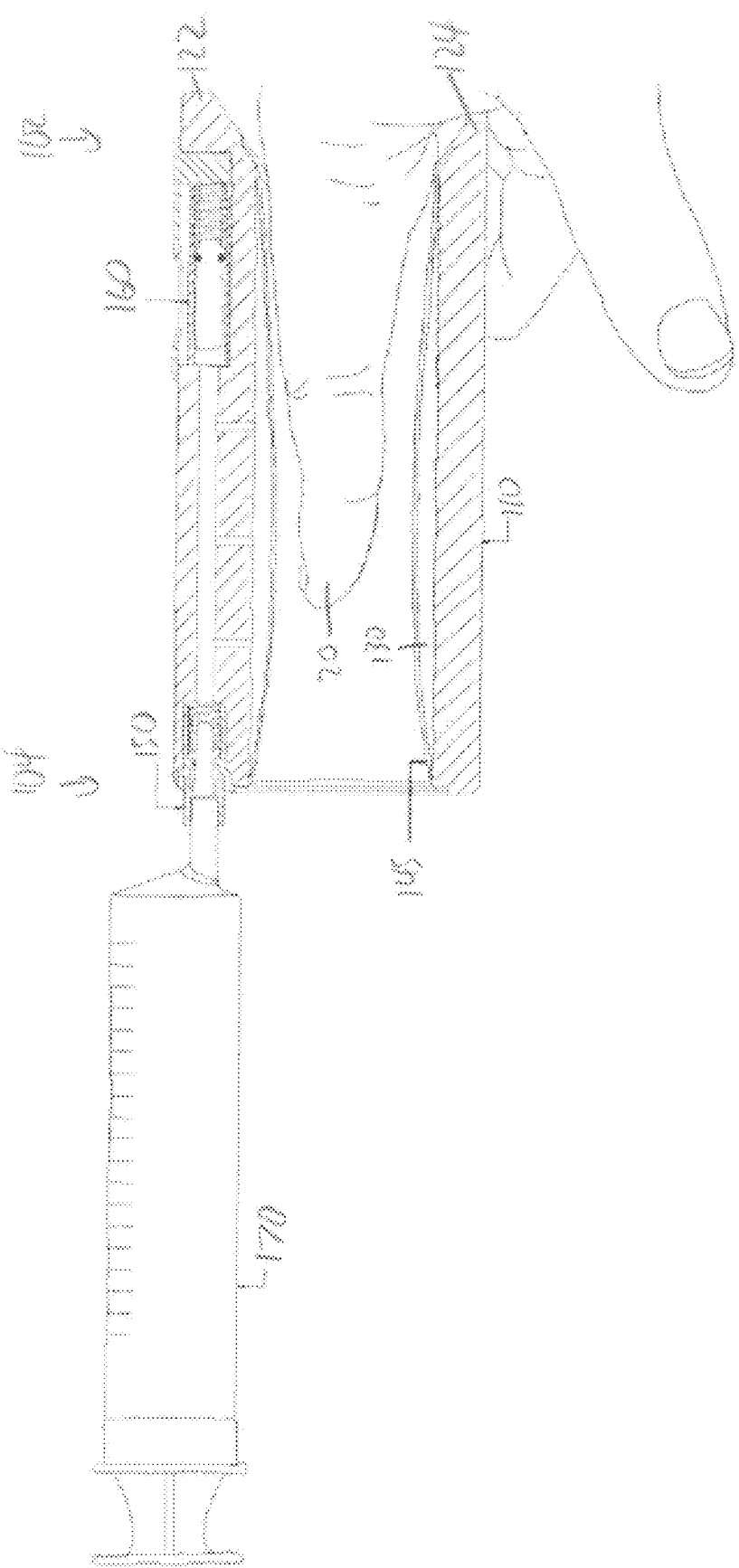
FIG. 9 is a schematic section view of the compression device of FIG. 4, with a source of pressurized fluid coupled to the compression device, and with a digit positioned in the digit cavity.
Figure 10:
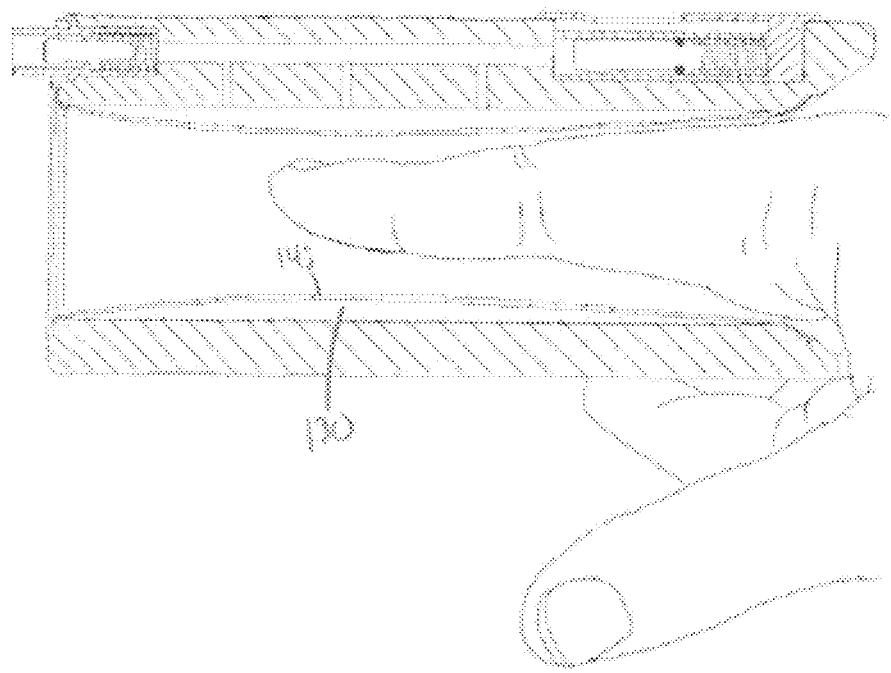
FIG. 10 is a schematic section view of the compression device of FIG. 4, with a digit positioned in the digit cavity and the inflation chamber in an uninflated state.

As shown in the example illustrated in FIG. 9, the compression device 100 is positioned relative to a digit 20 on which a ring (not shown) is stuck so that the digit is positioned in the digit cavity 120. Preferably, with the digit inserted, an interdigital fold (i.e. a web between adjacent digits) is adjacent or abuts at least one of the side portions 123a, 123b of the digit cavity opening 125. As noted above, the distally recessed side portion(s) allow(s) the compression device 100 to envelope most or substantially all of the inserted digit, allowing a compressing force to be applied to most or substantially all of the inserted digit.

Optionally, a lubricant may be provided on the outer surface of the digit to be inserted and/or on the inwardly facing surface of the flexible tubular sheet 145. The lubrication may assist with removing the ring after the finger has been compressed by device 100. Any suitable lubricant may be used.

As also shown in the example illustrated in FIG. 9, a source of fluid is coupled to the fluid inlet 150 of the compression device 100. The source of fluid may be used to introduce any suitable fluid, such as a liquid (e.g. cold water) or a gas (e.g. compressed air). In the illustrated example, the source of fluid includes a manually actuated syringe 170, although it will be appreciated that any suitable source of fluid may be used. For example, syringe 170 may be used to introduce e.g. cold water into the inflation chamber 130. Alternatively, a source of compressed air (e.g. a compressed air line, a manually operated pneumatic pump) may be used to introduce air or another suitable gas into the inflation chamber 130.

It will be appreciated that the digit may be positioned in the digit cavity 120 before, after, or concurrently with coupling of a source of fluid to the fluid inlet 150 of the compression device 100.

Where an auxiliary opening 127 is provided at the body distal end 104, the auxiliary opening 127 may be fully or substantially closed once a digit is positioned in the digit cavity 120. For example, a piece of rigid pipe or other suitable blocking member (not shown) may be positioned in the auxiliary opening 127 to inhibit or prevent the flexible bladder 140 from exerting a significant axial force on the distal end of an inserted digit. For example, once a digit has been positioned in the digit cavity 120, a blocking member may be inserted through the auxiliary opening 127 and advanced until it is adjacent or abutting the distal tip of the inserted digit.

Figure 11:
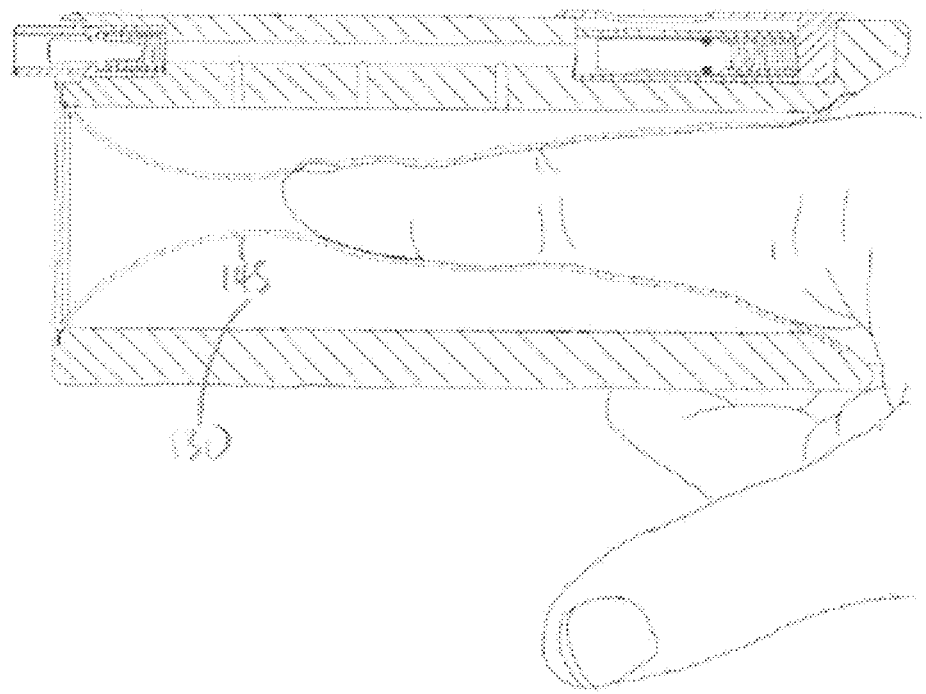
FIG. 11 is a schematic section view of the compression device and digit of FIG. 11, with the inflation chamber in a partially inflated state.
Figure 12:
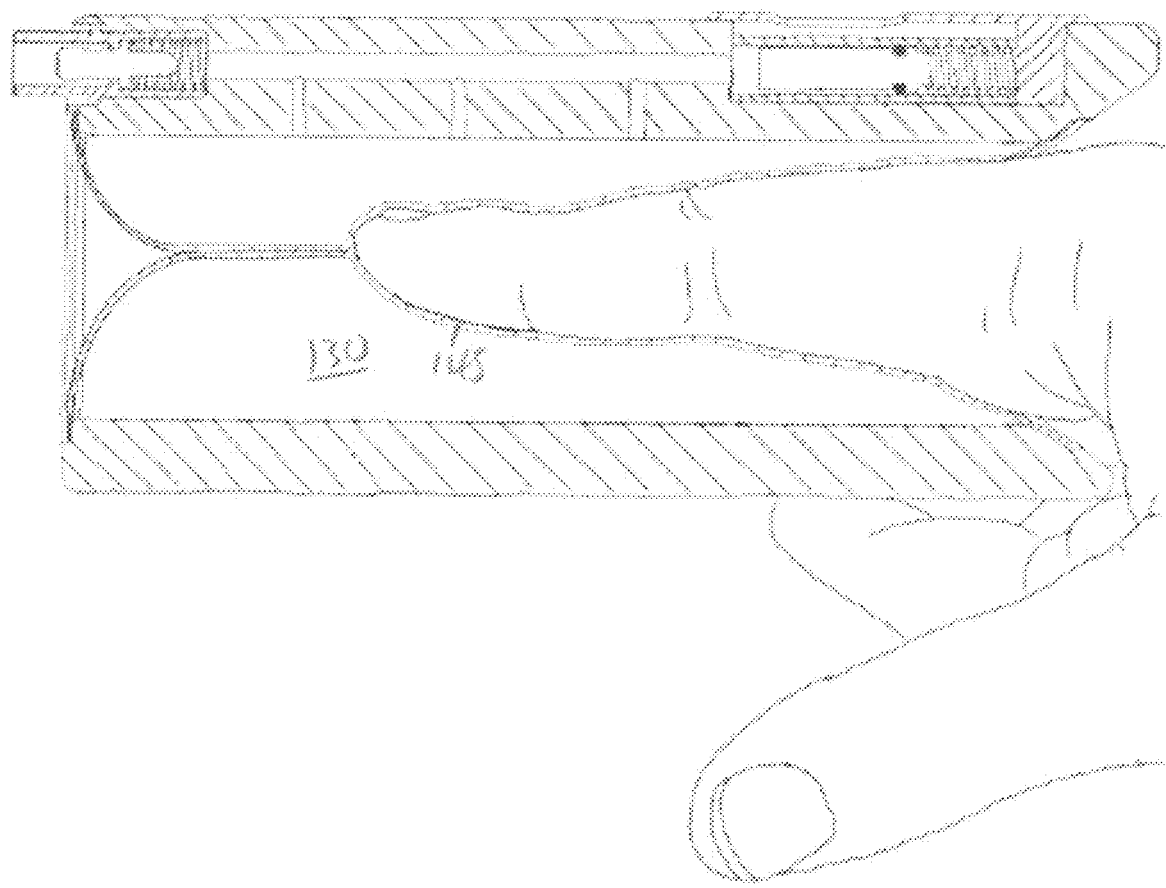
FIG. 12 is a schematic section view of the compression device and digit of FIG. 11, with the inflation chamber in an inflated state.

Once the digit is positioned in the digit cavity 120 and a source of fluid is coupled to the fluid inlet 150, e.g. as shown in FIG. 9, fluid may be introduced into the inflation chamber 130. (For ease of illustration, the source of fluid is not shown in FIGS. 10 to 12.) As illustrated in FIG. 11, the continued introduction of fluid into the inflation chamber 130 results in the interior wall 147 of the flexible bladder 140 being urged towards and into contact with the digit. Once the inflation chamber 130 has expanded to fill substantially all of the digit cavity (e.g. as illustrated in FIG. 12), further introduction of fluid into the inflation chamber 130 results in an increased pressure being applied to the exterior of the digit by the interior wall 147 of the flexible bladder 140.

Once the pressure in the inflation chamber 130 is within a target pressure range and/or has reached a target pressure, the introduction of fluid into the inflation chamber may be halted. The target pressure range and/or target pressure may be selected to promote a (net) flow of endemic fluid from the digit into the hand/foot and/or surrounding tissue, without causing damage to the tissue of the digit and/or causing excessive discomfort. For example, the target pressure may be from approximately 0 to 350, mmHg, or about 300 mmHg. The target pressure is preferably between 150 mmHg and 550 mmHg. This pressure range is generally sufficient to produce the targeted digit compression in a reasonable period of time, while mitigating harm or discomfort to the wearer. While the application of higher pressures (e.g. up to 800 mmHg) to an inserted digit may promote a marginally higher (net) flow of endemic fluid, it is thought that such increases in flow rate will be minor. It is also expected that there may be significant discomfort associated with the application of such elevated pressures, which may make their application undesirable. Still in some circumstance, such higher pressures may be employed as required.

For example, where a pressure gauge, such as fluid pressure gauge 160, is provided, fluid may be introduced into the inflation chamber 130 until the pressure gauge provides an indication that a desired pressure has been reached. For example, using the example illustrated in FIG. 13, fluid may be introduced into the inflation chamber until the line 166 is aligned with the "OK" reference mark 163 provided adjacent the viewing window 169. Patient discomfort may also be a consideration in determining when a suitable pressure has been reached.

Once a desired pressure has been reached, the compression device may remain on the digit for a length of time (e.g. at least 1 minute). During this time, the sustained application of pressure to the digit may force endemic fluid from the digit into the hand/foot and surrounding tissue, thereby reducing the volume and/or the maximum diameter of the digit.

As the volume of the digit is reduced, the pressure applied to the digit by the compression device may be reduced. A reduction in pressure may lead to a reduced (net) flow rate of endemic fluid, which may lessen the amount of fluid the compression device 100 can remove from the digit in a given time period. Preferably, a pressure gauge, such as fluid pressure gauge 160 may be monitored during the digit compression. If the pressure is observed to drop below an acceptable threshold, additional fluid may be introduced into the inflation chamber to return the pressure to the target pressure and/or to within the target pressure range.

After pressure has been applied to the digit for a desired period of time, and/or once the volume of the digit has been reduced to a target level, fluid may be removed from the inflation chamber and the digit subsequently removed from the digit cavity 120. For example, a collapsed syringe 170 may be used to evacuate fluid from the inflation chamber via the fluid inlet 150. For rapid pressure relief, the plunger of syringe 170 may be removed while the syringe remains coupled to the fluid inlet 150, allowing the inflation chamber to vent to atmosphere via the syringe body. Alternatively, the source of fluid may be decoupled and the check valve 151 may be depressed or otherwise actuated to allow the inflation chamber 130 to vent to atmosphere.

Once the digit is removed from the inflation chamber, distal traction should be immediately applied to the (formerly) 'stuck' ring in an effort to slide the ring towards and ultimately past the distal end of the digit. The reduced diameter of the digit should facilitate removal of the ring.

If the ring remains stuck, the digit may be re-positioned in the digit cavity, and the inflation chamber re-inflated in order to increase the amount and/or duration of pressure applied to the digit.

Figure 16:
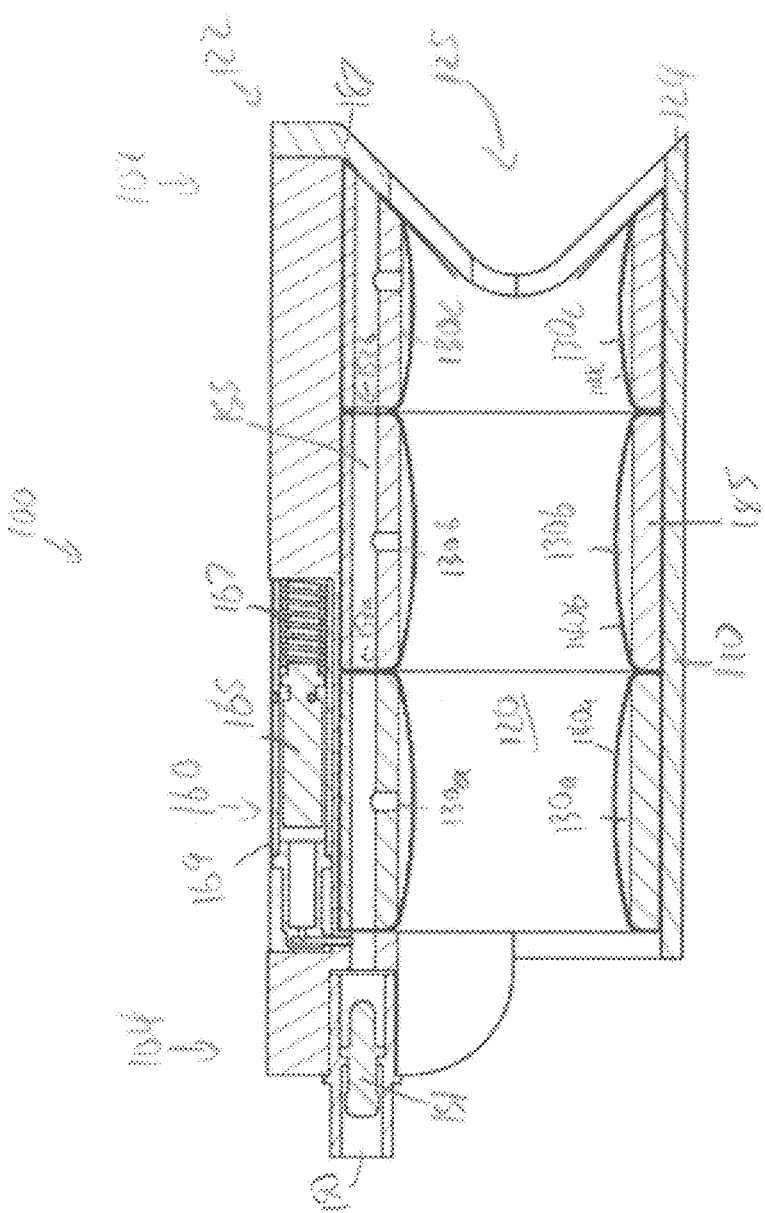
FIG. 16 is a section view of the compression device of FIG. 14, taken along line 16-16 in FIG. 15.
Figure 15:
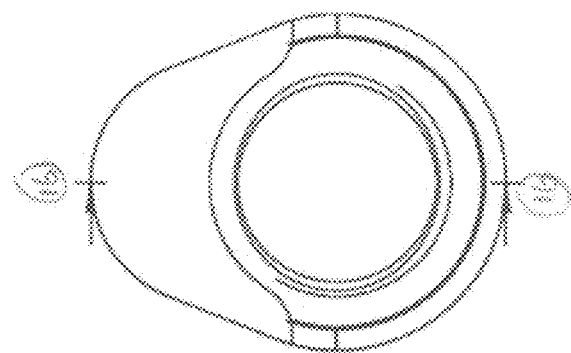
FIG. 15 is an end view of the proximal end of the compression device of FIG. 14.

FIGS. 14 to 18 illustrate an alternative embodiment of a compression device 100. In this example, three inflation chambers are provided in the digit cavity. As shown in FIG. 16, the inflation chambers are longitudinally spaced along the digit cavity 120, with a distal inflation chamber 130*a* comprising a distal bladder 140*a* positioned at the body distal end 104, a proximal inflation chamber 130*c* comprising a proximal bladder 140*c* positioned at the body proximal end 102, and a central inflation chamber 130*b* comprising a central bladder 140*b* positioned between the distal inflation chamber 103*a* and the proximal inflation chamber 130*c*. Alternatively, only two inflation chambers may be provided (e.g. a distal inflation chamber positioned adjacent a proximal inflation chamber). Alternatively, four or more inflation chambers may be provided.

Each inflation chamber 130*a* to 130*c* may be in fluid communication with the fluid inlet 150 of the compression device 100 via a fluid flow path 155. In this way, fluid introduced to the compression device 100 via the fluid inlet 155 may be directed towards the interior of each inflation chamber 130*a*, 130*b*, 130*c*.

Figure 20:
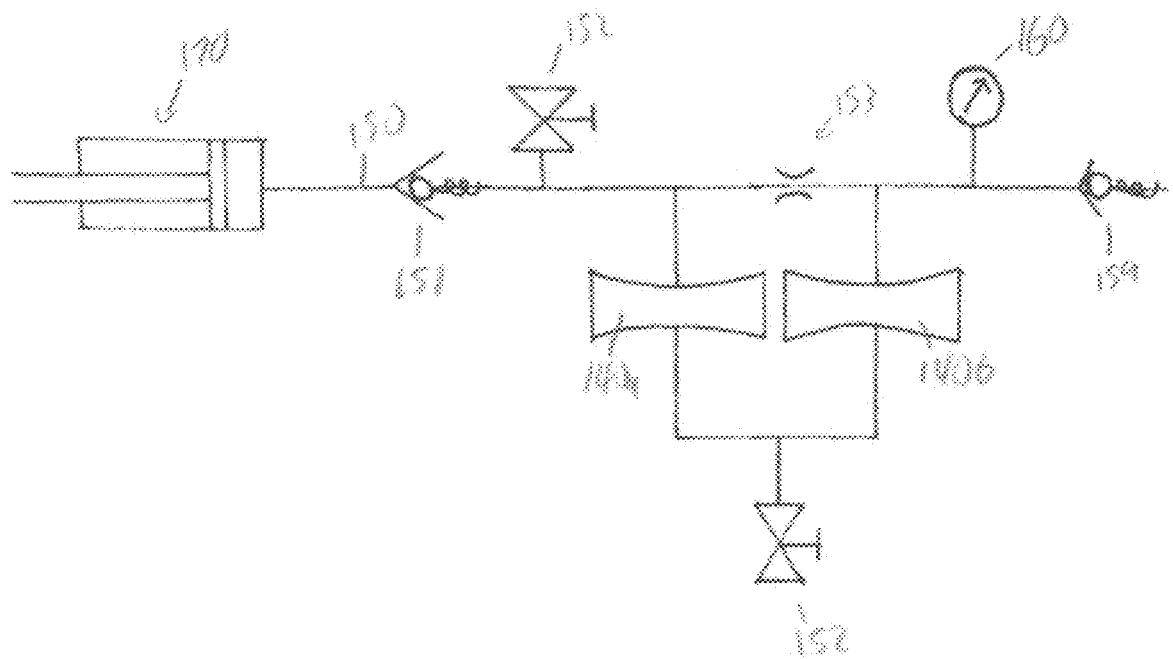
FIG. 20 is a schematic example of another pressure circuit of a compression device.

Optionally, one or more valves or other flow control devices may be provided to control a flow of fluid to the inflation chambers. For example, in the illustrated example a first orifice plate 153*a* is provided in the fluid flow path between the fluid inlet 150 and the central inflation chamber 130*b*, and a second orifice plate 153*b* is provided in the fluid flow path between the central inflation chamber 130*b* and the proximal inflation chamber 130*c*. As another example, in the schematic pressure circuit example shown in FIG. 20, an orifice plate 153 is provided between the fluid inlet 150 and the proximal bladder 140*b*.

An advantage of providing flow control devices in the fluid flow path 155 is that as fluid is introduced to the device via the fluid inlet 150, the first orifice plate 153*a* may restrict the flow rate of fluid along the fluid flow path, causing the flow rate into the distal inflation chamber 130*a* to be greater than the flow rate of fluid to the central inflation chamber 130b. Similarly, the second orifice plate 153b may restrict the flow rate of fluid along the fluid flow path, causing the flow rate into the central inflation chamber 130b to be greater than the flow rate of fluid to the proximal inflation chamber 130c. In this way, a positive pressure gradient may be developed along the length of the digit from the distal end of the digit to the proximal end of the digit, which may inhibit or prevent endemic fluid from flowing towards the tip of the digit.

In one or more alternative embodiments, a separate fluid inlet may be provided for each inflation chamber 130a, 130b, and/or 130c. In such embodiments, fluid may be introduced to each inflation chamber in a manner suitable to promote a positive pressure gradient along the length of the digit.

Figure 17:
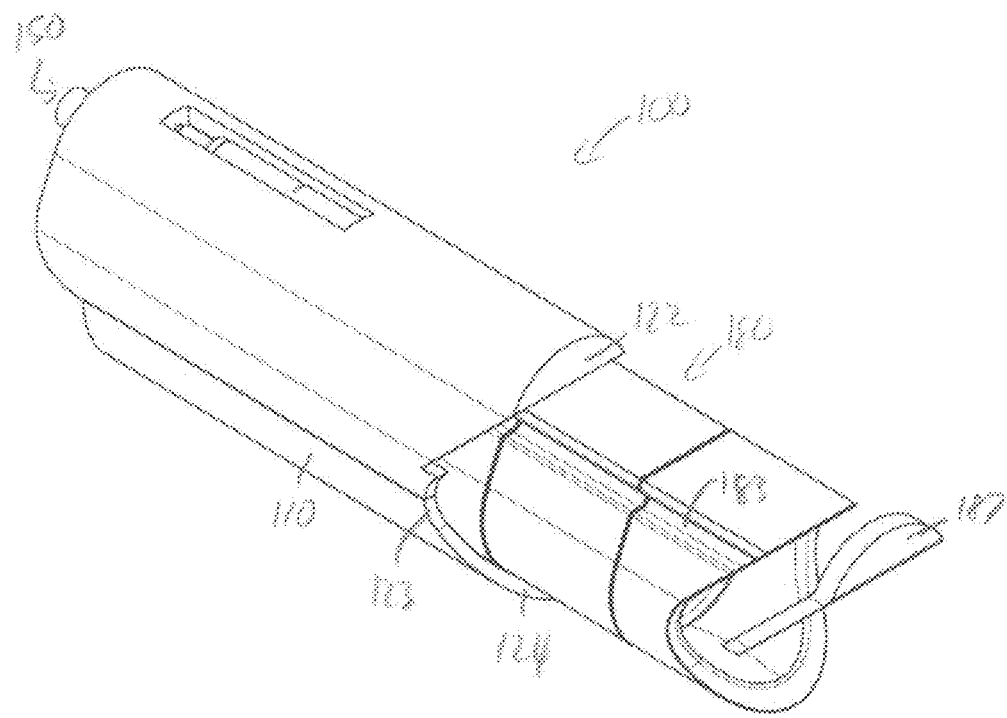
FIG. 17 is a perspective view of the compression device of FIG. 14, with the flexible bladders partially removed from the digit cavity.
Figure 18:
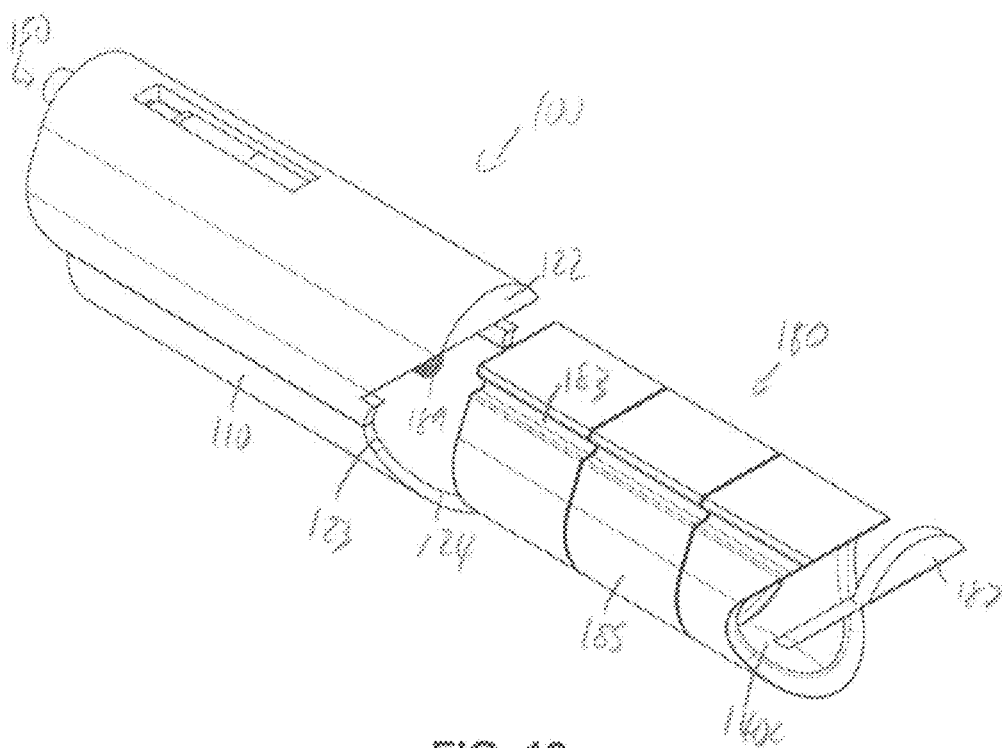
FIG. 18 is a perspective view of the compression device of FIG. 14, with the flexible bladders removed from the digit cavity.

Optionally, one or more flexible bladders 140 may be removably secured within the body or housing 110 of the compression device. For example, as illustrated in FIGS. 16 to 18, a removable bladder element 180 may include a flexible tubular bladder 140 and a rigid bladder mounting portion 185. Optionally, a portion of the fluid flow path 155 may be provided in the rigid bladder mounting portion 185. In the illustrated example, the rigid bladder mounting portion 185 has an engagement feature in the form of a longitudinal groove 183 that cooperates with a complementary engagement feature in the form of a longitudinal ridge (not shown) to facilitate the insertion and/or removal of the removable bladder element 185. An optional removable bladder retaining member 187 may be provided to retain bladder element 180 in an inserted position. An optional biasing member such a spring 189 may be provided to urge the bladder element 180 to a partially removed position upon removal of retaining member 187.

An advantage of providing one or more removable bladders is that the bladder element 180 may be removed and optionally disposed after the device has been used on a digit of a first patient, and new or cleaned bladder element 180 may be installed in the device 100 prior to its use on a patient and/or second digit. This may reduce operational cost associated with use of the device, as the housing and/or pressure monitoring system may be reused. This design may also improve the sanitation of the device, so that the device complies with various health and safety regulations (which may vary from jurisdiction to jurisdiction).

Figure 21:
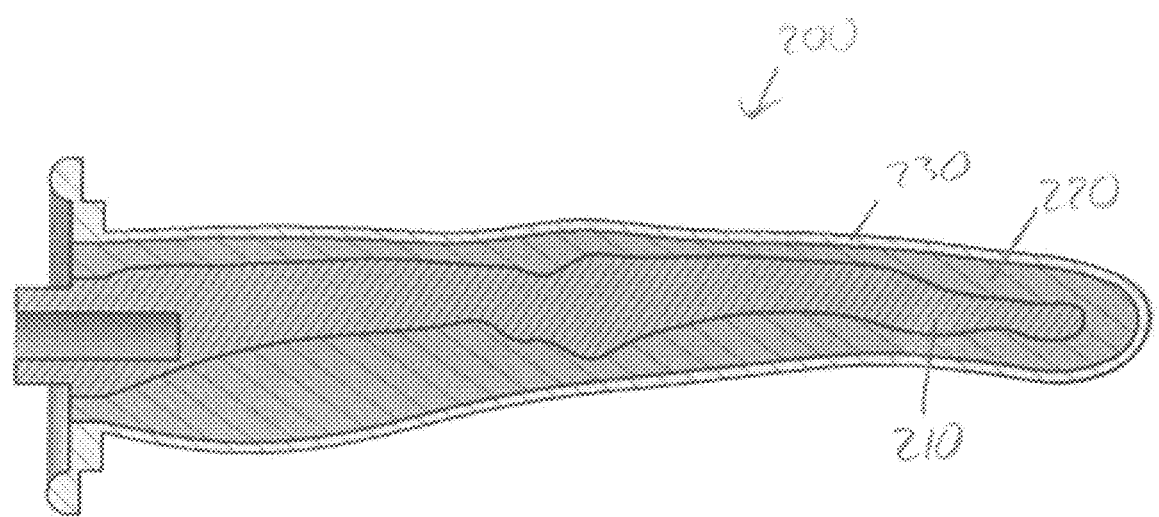
FIG. 21 is a schematic cross section of a testing model of a digit used to assess a digit compressing device.

Referring to FIG. 21, in order to assess the functionality of a digit compressing device similar to device 100, a testing model was developed to simulate the difficulties encountered by doctors in the ER without involving human testing. The testing model, an analogue for a human digit, was made using a 3-part urethane casting technique developed specifically for this application. As shown in FIG. 21, a hard urethane 210 was used for the bone, a soft open-cell foam 220 was used for the intermediary flesh, and a thin urethane rubber 230 with mechanical properties similar to that of human skin was used for the outer skin of the model 200. Water was used to simulate blood and edema flow through the open cell foam.

Several medical professionals with training in conventional ring removal techniques attempted to remove entrapped rings from the model using both conventional techniques and a digit compressing device similar to device 100.

Testing indicated that the digit compressing device did not cause lacerations to the outer skin of the testing model 200. In contrast, the conventional string method occasionally caused lacerations to the test model. Medical professionals confirmed that lacerations occasionally occur using the string method on patients, suggesting the testing model was a suitable analogue. This also suggests that removing a ring using compression device 100 may in some cases be safer than conventional ring removal methods.

Testing also indicated that use of the digit compressing device resulted in more rapid removal of stuck rings. For example, the engagement time (i.e. the time until compression of the digit was effected) for the tested device was lower than for the conventional string method. Also, the volume of fluid evacuated from the digit model using the tested devise was greater than for the conventional string method.

Reference is now made to FIGS. 27-28, which show a compression device 100 in accordance with another embodiment. In some cases, a ring stuck on a digit may have a tall profile. For example, engagement rings and the like often include settings with solitaire diamonds that stand tall from the underlying band. It may be uncomfortable for the wearer if pressure is applied to such rings by an inflating bladder. Moreover, it may be difficult for the bladder to stretch sufficiently to conform to such rings. The illustrated embodiment of compression device 100 is designed to be worn on the wearer's digit 20 adjacent the stuck ring 10. In use, compression device 100 may compress a portion of the digit 20 that is adjacent to and distal of the stuck ring 10. This can allow compression device 100 to operate on rings that have a profile unsuitable for full-digit compression.

Figure 32:
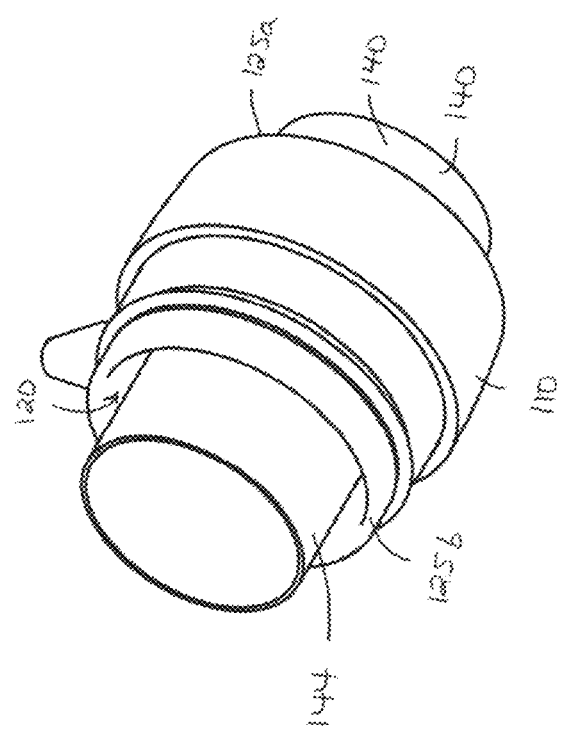
FIG. 32 is a perspective view of the device body of FIG. 30 with a tubular bladder inserted.
Figure 31:
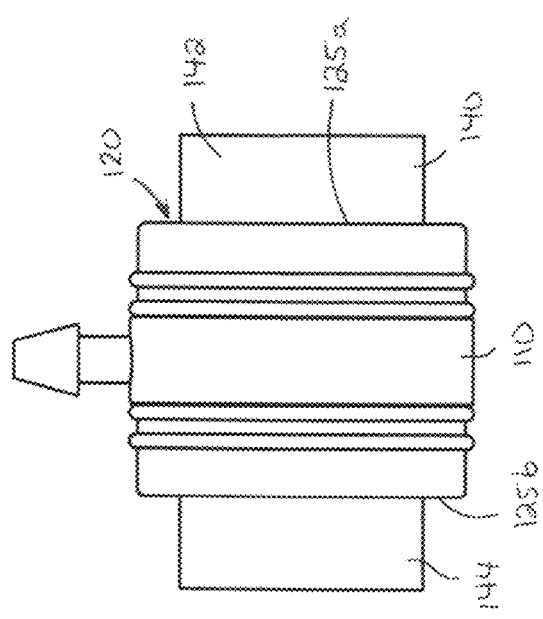
FIG. 31 is a side elevation view of the device body of FIG. 30 with a tubular bladder inserted.

In some embodiments, compression device 100 may include a removable bladder. FIGS. 29-33 show steps for installing a new bladder into compression device 100. Beginning with FIGS. 29-30, bladder engagement members 348 may be disengaged (e.g. disconnected) from body 110. FIGS. 31-32 show inserting a tubular bladder 140 into digit cavity 120. As shown, proximal bladder portion 142 may protrude from cavity proximal opening 125a, and distal bladder portion 144 may protrude from cavity distal opening 125b. Turning to FIG. 33, proximal bladder portion 142 is shown folded over body proximal end 102 so that proximal bladder portion 142 overlies body exterior surface 320. Although not shown, the distal bladder portion is similarly folded over the body distal end so that the distal bladder portion overlies body exterior surface 320.

Finally, FIG. 34 shows bladder engagement members 348 re-engaged with body 110. As shown, bladder engagement members 348 act to compress (i.e. exert compressive force upon) proximal and distal bladder portions 142, 144 against body 110. This creates a fluid tight seal for the annular inflation chamber 130, which is defined between body inner surface 126 and bladder 140. Body 110 may include a fluid inlet 150 that is fluidly connected to annular inflation chamber 130. In use, fluid (e.g. liquid or gas) may be forced into annular inflation chamber 130 through fluid inlet 150 to inflate inflation chamber 130, whereby pressure is exerted by bladder 140 against a digit extending within digit cavity 120.

An advantage to this design is that it allows a tubular bladder 140 to be easily inserted and sealed for use in removing a ring, and afterwards removed and discarded (or sanitized for reuse).

FIGS. 41-44 show steps for installing a new bladder in a compression device 100, in accordance with at least one embodiment. Beginning with FIG. 41, bladder engagement members 348 may be disengaged. FIG. 42 shows a tubular bladder 140 having gaskets 352 inserted into digit cavity 120. As shown, proximal bladder portion 142 may protrude from cavity proximal opening 125a, and distal bladder portion 144 may protrude from cavity distal opening 125b. Turning to FIG. 43, proximal bladder portion 142 is shown folded over body proximal end 102 so that proximal bladder portion 142 overlies body exterior surface 320. Similarly, distal bladder portion 144 is shown folded over body distal end 104 so that distal bladder portion 142 overlies body exterior surface 320. Finally, FIG. 44 shows bladder engagement members 348 re-engaged with body 110, such that they create a fluid tight seal between the proximal and distal bladder end portions and the body. As shown in FIG. 43, body 110 may include retainers 402 (e.g. proximal retainer 402*a* and distal retainer 402*b*) that help secure engagement members 348 in place when engaged with body 110. Retainers 402 may be any member suitable for increasing the retaining force of engagement members 348 on body 110, while maintaining the non-destructive removable connection. For example, retainers 402 may be protrusions from exterior surface 320 that mate with engagement members 348 when engaged with body 110.

Body 110 can have a short length (e.g. 10 mm to 50 mm) intended to allow a distal end of the digit to protrude from cavity distal opening 125*b*, or an extended length (e.g. greater than 50 mm, such as 50 mm to 150 mm) intended to extend to or beyond a distal end of the digit. An advantage of a short body 110 is that it may cost less to manufacture, and may be less constraining on the wearer. An advantage of an extended body 110 is that it may provide compression all the way to the distal tip of the wearer's digit. This may mitigate discomfort some wearer's experience at the distal tip of their digit when the distal end of the digit is not also compressed in the procedure.

Referring to FIG. 34, compression device 100 may include one or many bladder engagement members 348 that collectively act to seal the bladder proximal and distal end portions 142, 144 to body 110. In the illustrated example, compression device 100 is shown including a proximal bladder engagement member 348*a* for bladder proximal end portion 142, and a distal bladder engagement member 348*b* for bladder distal end portion 144.

Referring to FIGS. 30 and 34, each bladder engagement member 348 may have any design suitable to create a fluid tight seal when engaged with body 110 and a bladder portion 142, 144, and to allow a bladder portion 142, 144 to be removed from body 110 when disengaged. For example, a bladder engagement member 348 may have an annular body that overlies a portion of body 110 and bladder 140 when in an engaged position. This allows bladder engagement member 348 to exert a radially inward force upon bladder 140 and body 110 that may form a fluid tight seal between bladder 140 and body 110. In the illustrated embodiment, each bladder engagement member 348 is formed as a removable annular end cap. For example, end caps 348 may be engaged by forcing end caps 348 axially over end portions of body 110. End caps 348 may be retained in engagement by friction until the user forceably (but non-destructively) disconnects end caps 348 from body 110. In some embodiments, bladder engagement members 348 may connect to body 110 by mating threads or other means.

In some embodiment, bladder engagement members 348 may remain connected to body 110 in both the engaged and disengaged position. For example, bladder engagement members 348 may be pivotably connected to body 110, and may pivot between engaged and disengaged positions.

In some embodiments, the fluid tight seal formed when bladder engagement member(s) 348 are engaged may be assisted by one or more gaskets (e.g. that is compressed by bladder engagement member(s) 348 when engaged). FIG. 30 shows an example in which body 110 includes gaskets 352 which encircle body exterior surface 320 at body proximal and distal end portions 356, 360. In use, bladder proximal and distal end portions 142, 144 (FIG. 34) may overlie respective gasket(s) 352, and bladder engagement members 348 may compress bladder portions 142, 144 (FIG. 34) against gaskets 352 to form fluid tight seals.

Referring to FIG. 34, alternatively or in addition to body 110 having gasket(s) 352, each bladder engagement member 348 may include one or more gaskets 352 as shown. In use, gaskets 352 may be compressed against bladder portions 142, 144 to form fluid tight seals.

Referring to FIGS. 33 and 35, alternatively or in addition to body 110 and/or bladder engagement members 348 having gasket(s), bladder portions 142, 144 may have gaskets 352 (shown in FIG. 33). As shown, bladder gaskets 352 may be integrally formed with or connected to bladder portions 142, 144, and may have a thickness which is greater than the adjacent bladder material. Bladder gaskets 352 may be located at the terminal ends of bladder 140 as shown, or inboard of the bladder terminal ends. In use, bladder gaskets 352 may be compressed by bladder engagement members 348 against body 110 to form fluid tight seals.

Referring to FIGS. 27-28, fluid inlet 150 may be fluidly connected to a fluid source 170 to receive pressurized fluid (e.g. liquid or gas) into the inflation chamber. Fluid source 170 can be any source of pressurized fluid, whether manually or power operated, that is suitable for inflating the inflation chamber to the target inflation pressure. For example, fluid source 170 may be a syringe as illustrated in FIG. 9, or may be a power operated pump (e.g. liquid pump or air compressor) as shown. As shown, fluid source 170 may be connected to inlet 150 by a fluid conduit 364. In the illustrated example, fluid conduit 364 is a flexible hose. An advantage of this design is that it may permit the wearer some freedom to move the associated hand/foot about while the procedure is taking place. In alternative embodiments, fluid conduit 364 may be a rigid conduit, which may be more durable.

Figure 36:
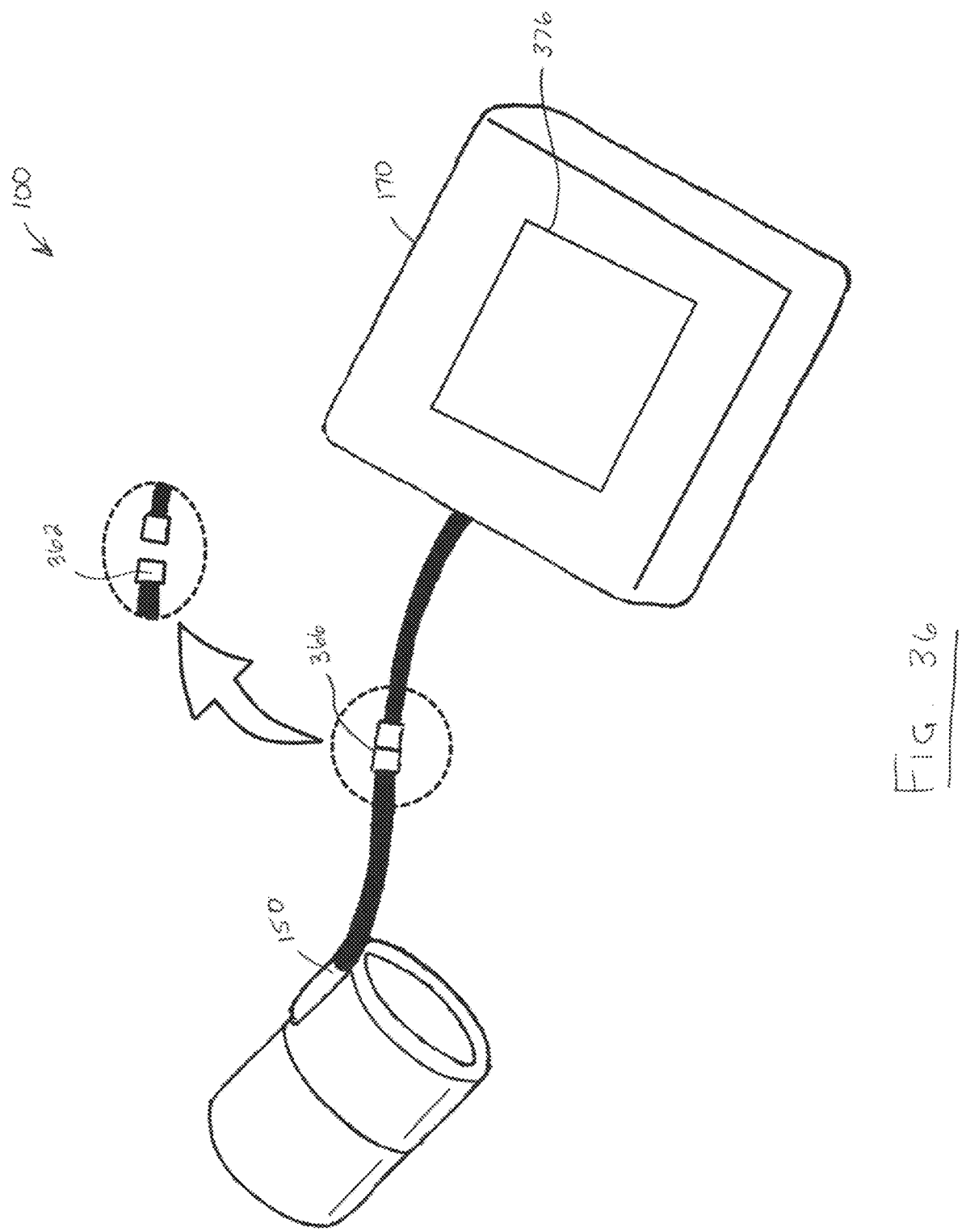
FIG. 36 is a perspective view of a digit compression device connected to a fluid source in accordance with another embodiment.
Figure 37:
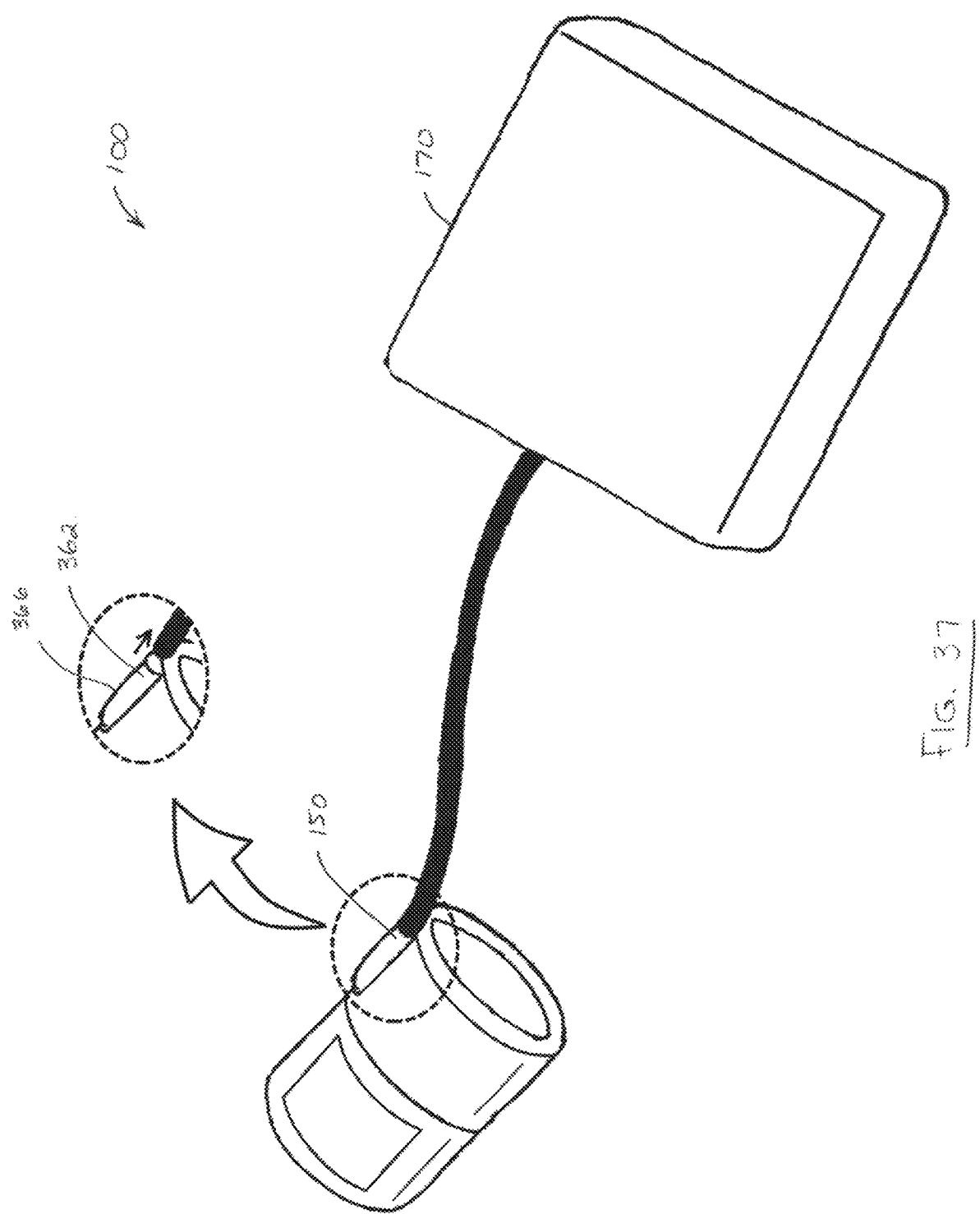
FIG. 37 is a perspective view of a digit compression device connected to a fluid source in accordance with another embodiment.

Turning to FIGS. 36 and 37, the fluid flow path between fluid source 170 and the inflation chamber may include a valve 362—i.e. valve 362 may be located upstream of the inflation chamber. Valve 362 may be opened to allow passage of pressurized fluid into the inflation chamber, and sealed to seal pressurized fluid in the inflation chamber. An example of valve 362 is check valve 151 shown in FIGS. 16, 19, and 20. Valve 362 may be opened while pressurizing the inflation chamber, and sealed after a predetermined fluid pressure has been reached. Valve 362 may remain sealed for a prescribed time period (e.g. at least 1 minute, such as 3 minutes to 10 minutes) before venting the inflation chamber. For example, fluid source 170 may be disconnected from compression device 100 (e.g. by disconnecting fluid conduit 364 or an associated connector) while valve 362 is sealed, thereby allowing the wearer to freely move about for the prescribed time period until the compression procedure is completed. For example, the wearer may undergo the ring removal procedure at a jewelry store, and may leisurely wander the store—disconnected from fluid source 170—during a hold period while compression device 100 continues to compress their digit for a prescribed period of time. When the hold time period has elapsed, the operator (e.g. jewelry store clerk) may attend to venting the pressurized gas from the inflation chamber (e.g. by opening valve 362), and then removing the stuck ring from the compressed digit.

In some embodiments, a fluid conduit connector 366 located upstream of fluid inlet 150 (e.g. as in FIG. 36) or located at fluid inlet 150 (e.g. as in FIG. 37). Fluid conduit connector 366 may be separate from valve 362, or may include valve 362. Where fluid conduit connector 366 includes valve 362, fluid conduit connector 366 may seal automatically upon disconnection (e.g. the integrated valve 362 may be a one-way valve, such as a check valve or similar), or may be manually sealed prior to disconnection (e.g. the integrated valve 362 may include a manually operated valve actuator). By providing a fluid tight seal when disconnected, fluid conduit connector 366 may retain the pressurized fluid in the inflation chamber. This can allow the wearer complete freedom to move away from fluid source 170 while they wait a prescribed time period for the compression procedure to be completed.

Figure 38:
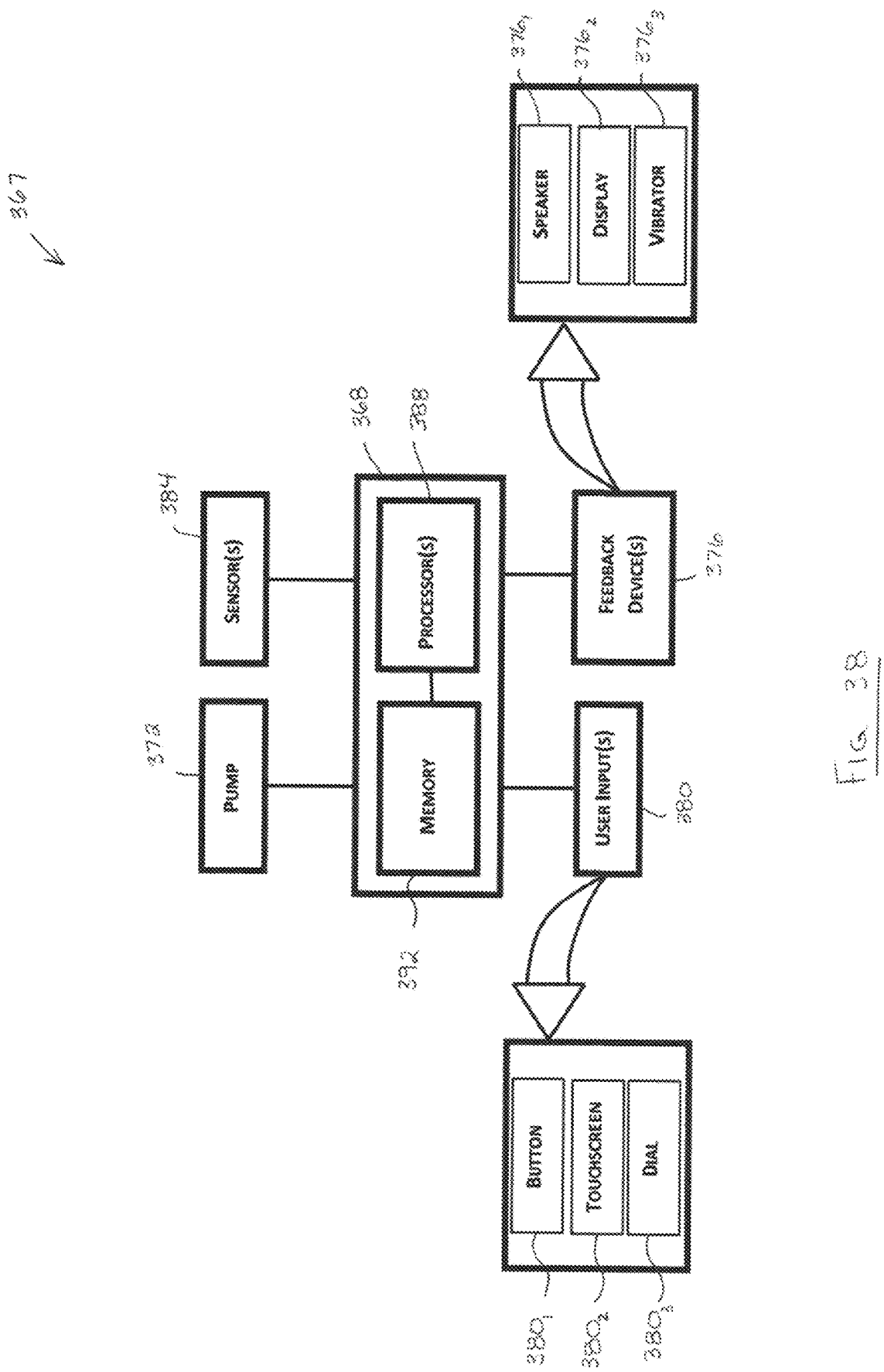
FIG. 38 is a schematic illustration of an electronic control system in accordance with an embodiment.

Reference is now made to FIGS. 27 and 38. In some embodiments, compression device 100 includes an electronic control system 367. As shown, electronic control system 367 may include a controller 368 that is configured to direct the operation of a pump 372 and/or feedback device(s) 376, and/or may be responsive to user input(s) 380 and sensor(s) 384. For example, controller 368 may receive an activation signal from a user input 380 and in response direct pump 372 to activate whereby pump 372 supplies pressurized fluid into the inflation chamber. Controller 368 may receive from sensor 384 (e.g. a pressure sensor) signals indicative of the pressure within inflation chamber, and in response direct a feedback device 376 (e.g. an electronic display) to provide an indication of the current pressure and/or progress made towards a target pressure. When controller 368 receives signals from sensor 384 indicating that the predetermined target pressure within the inflation chamber has been reached, controller 368 may direct pump 372 to deactivate. Controller 368 may further direct feedback device 376 to provide an indication of time remaining of a prescribed hold period. For example, controller 368 may direct feedback device 376 to alert the wearer that the prescribed hold period has elapsed. The inflation chamber may then be vented, the compression apparatus removed 100 from the compressed digit, and then stuck ring removed from the compressed digit.

Controller 368 may include one or more processors 388 and memory 392. Processor 388 may be any processing device suitable for performing the functions described herein. For example, processor 388 may include one or more ARM™, RISC, Intel™, or AMD™ microprocessors, or integrated circuits (e.g. fixed or FPGA (field programmable gate array)).

Memory 392 may include volatile memory (e.g. RAM) and/or non-volatile memory (e.g. flash memory). Memory 392 may store computer executable instructions (also referred to as computer readable instructions) that when executed by the one or more processors 388, configure the one or more processors 388 to collectively perform the functions and methods described herein. Memory 392 may include local storage (connected by wire or wirelessly to processor 388), and/or remote storage (connected to processor 388 across a network, such as the Internet). Accordingly, as used herein and in the claims, content is "stored" in memory, where that content is stored in local storage or remote storage, or distributed across both local and remote storage, unless explicitly specified otherwise (e.g. "remotely stored" or "locally stored").

Sensor(s) 384 may be any device suitable for providing an indication of the fluid pressure within the inflation chamber to controller 368. For example, sensor(s) 384 may include a pressure sensor that is fluidly coupled to the inflation chamber within body 110. Controller 368 may continuously or intermittently receive signals from sensor(s) 384 indicative of the fluid pressure within the inflation chamber in order to direct the operation of feedback device(s) 376 to notify the user of the current fluid pressure and/or progress towards the target pressure (e.g. alert the user that the target fluid pressure has been reached).

Feedback device(s) 376 may be any devices that can provide auditory, visual, or haptic indicia to a user of progress in a digit compression procedure (e.g. current pressure, progress towards target pressure, or time remaining in a prescribed hold time). For example, feedback device(s) 376 may include a speaker $376_1$, an electronic display $376_2$ (e.g. LCD, LED, or OLED display), and/or a vibrator $376_3$ (e.g. an offset motor, a linear resonant actuator, and/or a piezo electric vibrator). Feedback device(s) 376 may be communicatively coupled to controller 368 by wire or wirelessly.

Speaker $376_1$ may indicate progress with spoken words, such as "one hundred millimeters mercury", "target pressure reached", "ten seconds remaining", or "hold time elapsed" for example. Alternatively or in addition, speaker may indicate progress with non-verbal sounds, such as sound frequency (e.g. pitch increases or decreases based on progress towards a target pressure or prescribed time period), sound pattern (e.g. pattern of tones or beeps that change based on pressure or time), and/or volume (e.g. volume increases or decreases based on pressure or time). Speaker $376_1$ may include a special alert (verbal or non-verbal) when the target pressure is reached or when the prescribed hold time has elapsed.

Figure 39:
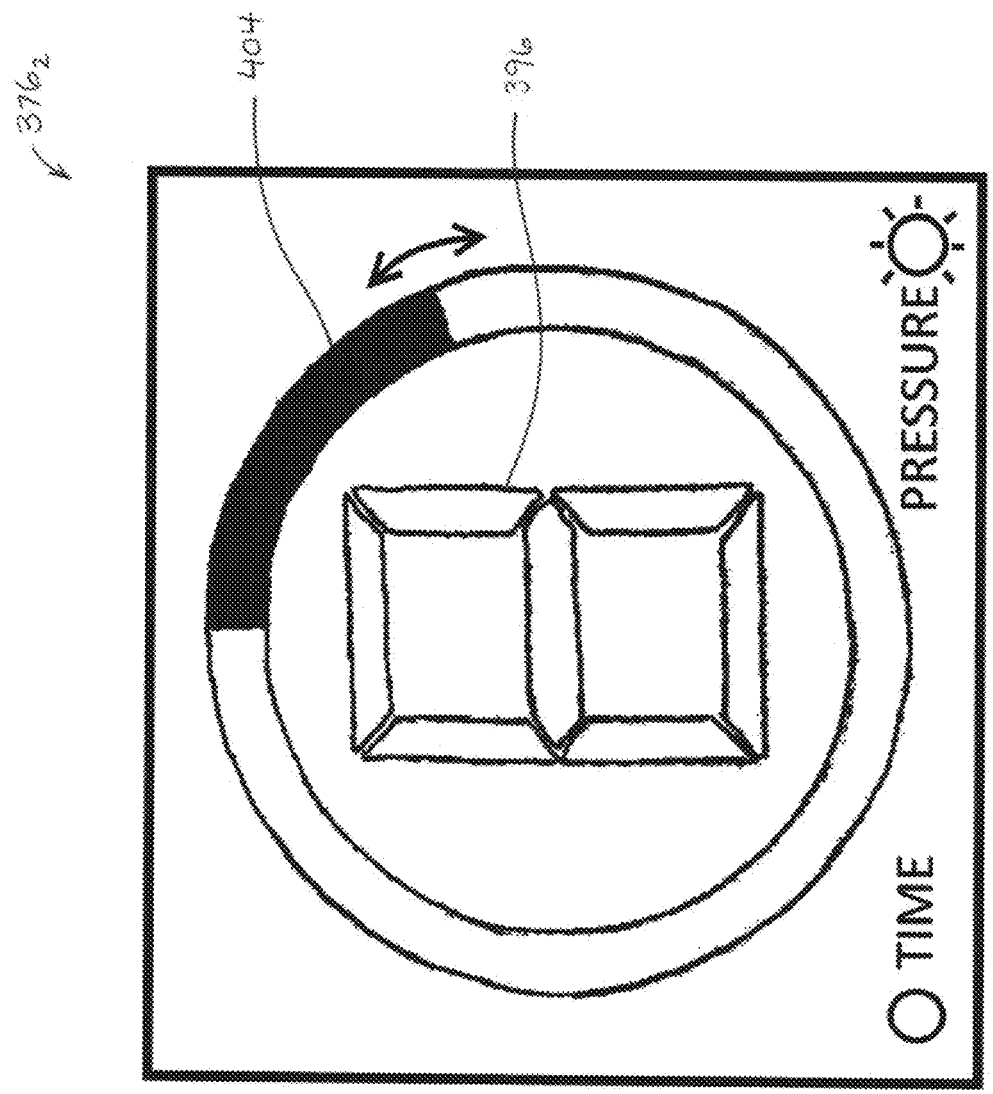
FIG. 39 is a schematic illustration of a display of the electronic control system of FIG. 38, showing progress in a digit compression procedure, in accordance with an embodiment.

Referring to FIG. 39, display $376_2$ may indicate progress in any visual form, such as with a numerical representation 396 (e.g. 1 minute, or 100 mm Hg) and/or a graphical representation 404 (a graph, color coding, or other non-numerical visual representation). Representations 396, 404 may indicate progress in absolute terms (e.g. current pressure or current time elapsed or remaining), or relative terms (e.g. percentage, patterned color coding, etc.).

Returning to FIG. 38, vibrator $376_3$ may indicate progress, in absolute or relative terms, in any manner, such as for example by vibration intensity, frequency of vibration pulses, or vibration pattern (e.g. Morse code, or similar).

User input(s) 380 may be any device that can receive input from a user, such as for example a button $380_1$, a touchscreen $380_2$, or a dial $380_3$. A user may interact with (e.g. manipulate) user input(s) 380 to signal commands to controller 368—such as to begin or stop a compression procedure, to set a target inflation pressure, and/or to set a prescribed hold time.

Referring to FIGS. 27 and 38, electronic control system 367 may be located entirely within fluid source 170, or electronic control system 367 may include two or more subsystems 408 distributed between fluid source 170, body 110, and/or external device(s) (e.g. a tablet or smartphone) that collectively form electronic control system 367. The subsystems 408 may be communicatively coupled to each other, by wire or wirelessly, to exchange signals. Still referring to FIGS. 27 and 38, FIG. 27 shows an example in which electronic control system 367 includes a subsystem $408_1$ in fluid source 170, and a subsystem $408_2$ in body 110. For example, subsystem $408_1$ may include a processor 388 and memory 392 of controller 368, as well as a pump 372 and optionally one or more (or all) of sensor(s) 384, user input(s) 380, and feedback device(s) 376. Subsystem $408_2$ may include another processor 388 and memory 392 of controller 368, as well as one or more (or all) of sensor(s) 384, user input(s) 380, and feedback device(s) 376. FIG. 28 shows an example in which an electronic display $376_2$ is mounted to body 110 for displaying progress in a digit compression procedure to the wearer. This provides the wearer with ready-information on the progress of the digit compression procedure. For example, the wearer could receive indications of the progress of a prescribed hold time (e.g. be notified when the hold period has elapsed) while they casually wander a jewelry store.

FIG. 36 shows an alternative embodiment in which all of the electronic control system 367 is located in fluid source 170. An advantage of this design is that it can reduce the size of body 110 as compared with designs that include additional components in or on body 110. This may make body 110 more comfortable for the wearer.

Figure 40:
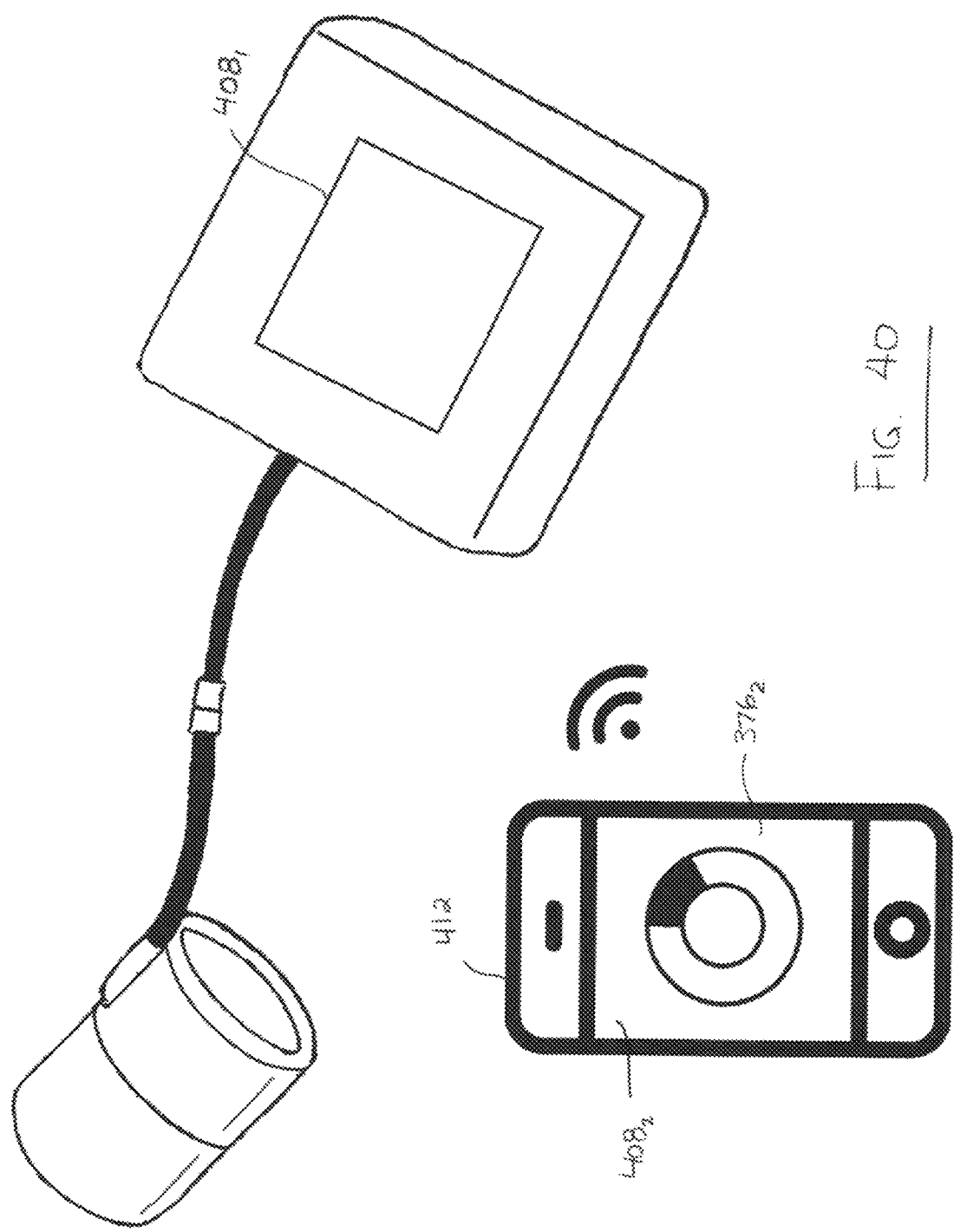
FIG. 40 is a perspective view of a digit compression device connected to a fluid source, and communicatively coupled to an external mobile device in accordance with another embodiment.

FIG. 40 shows another embodiment in which a portion of electronic control system 367 is located in an external device 412 (e.g. an external mobile device, such as a smartphone or tablet). For example, external device 412 may include a subsystem $408_2$ with another processor 388 and memory 392 of controller 368, as well as one or more (or all) of user input(s) 380, and feedback device(s) 376 (see FIG. 38). In the illustrated example, subsystem $408_2$ onboard external device 412 includes an electronic display $376_2$ for displaying progress in the digit compression procedure.

Returning to FIG. 38, in some embodiments controller 368 may store in memory 392 a bladder cycle counter, and increment the counter when a digit compression procedure is performed. This may permit the operator to track the number of uses of a bladder in cases where a bladder is reusable a prescribed number of times before it must be sanitized or replaced. Controller 368 may direct feedback device(s) 376 to provide an indication of the number of uses or remaining uses (e.g. controller 368 may direct feedback device(s) 376 to provide visual, auditory, and/or haptic indicia that a bladder should be replaced when the bladder cycle counter equals or exceeds a predetermined maximum number of cycles).

As used herein, the wording "and/or" is intended to represent an inclusive—or. That is, "X and/or Y" is intended to mean X or Y or both, for example. As a further example, "X, Y, and/or Z" is intended to mean X or Y or Z or any combination thereof.

While the above description describes features of example embodiments, it will be appreciated that some features and/or functions of the described embodiments are susceptible to modification without departing from the spirit and principles of operation of the described embodiments. For example, the various characteristics which are described by means of the represented embodiments or examples may be selectively combined with each other. Accordingly, what has been described above is intended to be illustrative of the claimed concept and non-limiting. It will be understood by persons skilled in the art that other variants and modifications may be made without departing from the scope of the invention as defined in the claims appended hereto. The scope of the claims should not be limited by the preferred embodiments and examples, but should be given the broadest interpretation consistent with the description as a whole.

Items

Item 1: A compression device for freeing a ring trapped on a digit, the compression device comprising:
  a rigid outer body extending from a body proximal end to a body distal end, the rigid outer body comprising:
    a digit cavity extending from a cavity opening at the body proximal end towards the body distal end,
    a fluid inlet, and
    a fluid flow path fluidly connecting the fluid inlet to one or more inflation chambers positioned in the digit cavity,
    wherein the body proximal end comprises an upper portion, a lower portion, and two laterally spaced-apart side portions, each of the side portions connecting the upper portion to the lower portion, at least one of the side portions being distally recessed as compared to the upper and lower portions to accommodate an interdigital fold; and
  at least one flexible bladder lining the digit cavity, each flexible bladder defining at least one wall of one of the inflation chambers.

Item 2: The compression device of any preceding item, wherein each of the side portions is distally recessed as compared to the upper and lower portions.

Item 3: The compression device of any preceding item, further comprising a fluid pressure gauge rigidly connected to the body and fluidly connected to the fluid flow path.

Item 4: The compression device of any preceding item, wherein the pressure gauge includes a pressure indicator movable in response to fluid pressure within the fluid flow path, and a visual indicium identifying a position of the pressure indicator corresponding to a target pressure.

Item 5: The compression device of any preceding item, wherein the pressure gauge is housed in the rigid outer body.

Item 6: The compression device of any preceding item, wherein the visual indicium is provided on the rigid outer body.

Item 7: The compression device of any preceding item, wherein the rigid outer body defines at least one wall of each of the inflation chambers.

Item 8: The compression device of any preceding item, wherein the digit cavity has a closed distal end.

Item 9: The compression device of any preceding item, wherein the fluid inlet is at the body distal end.

Item 10: The compression device of any preceding item, wherein the fluid inlet comprises a normally-closed valve that is openable by connecting a fluid source.

Item 11: The compression device of any preceding item, wherein the digit cavity has a substantially cylindrical cross-sectional shape.

Item 12: The compression device of any preceding item, wherein the upper and lower portions extend proximally of the two side portions.

Item 13: The compression device of any preceding item, wherein the at least one inflation chamber comprises a first inflation chamber and a second inflation chamber, and the compression device further comprises a flow control valve in the fluid flow path between the first inflation chamber and the second inflation chamber.

Item 14: The compression device of any preceding item, wherein the flow control valve is an orifice valve.

Item 15: The compression device of any preceding item, wherein the rigid outer body is at least one of translucent or transparent.

Item 16: The compression device of any preceding item, wherein at least one of the inflation chambers is at least one of translucent or transparent.

Item 17: The compression device of any preceding item, further comprising a pressure relief valve in fluid communication with the fluid flow path, and openable to atmosphere in response to a predetermined excessive fluid pressure within the fluid flow path.

Item 18: The compression device of any preceding item, wherein the flexible bladder comprises a tubular sheet extending from a sheet proximal portion to a sheet distal portion, each of the sheet proximal portion and sheet distal portion being sealed fluid tight to the rigid outer body.

Item 19: The compression device of any preceding item, wherein the at least one flexible bladder is removably coupled to the rigid outer body.

Item 20: The compression device of any preceding item, wherein the rigid outer body has an exterior surface, and the exterior surface has at least one lateral concavity extending distally from one of the side portions of the body proximal end.

Item 21: The compression device of any preceding item, wherein the rigid outer body has an exterior surface, and the exterior surface has a lateral concavity extending distally from each of the side portions of the body proximal end.

Item 22: The compression device of any preceding item, wherein one of the side portions of the body proximal end extends proximally of the other of the side portions of the body proximal end.

Item 23: A compression device for freeing a ring trapped on a digit, the compression device comprising:
  a rigid outer body extending from a body proximal end to a body distal end, the rigid outer body comprising: a digit cavity extending from a cavity proximal opening at the body proximal end to a cavity distal opening at the body distal end, and
  a fluid inlet; and
  a removable flexible tubular bladder extending from a lining proximal end to a lining distal end, the bladder including a bladder intermediate portion joining a bladder proximal portion to a bladder distal portion, the bladder intermediate portion located inside the digit cavity.
  wherein each of the bladder proximal portion and the bladder distal portion are removably sealed to the rigid outer body to define an annular inflation chamber inside the digit cavity between the bladder and the rigid outer body, the fluid inlet being fluidly connected to the annular inflation chamber.

Item 24: The compression device of any preceding item, wherein:
  the bladder proximal portion overlies the body proximal end, and the bladder distal portion overlies the body distal end.

Item 25: The compression device of any preceding item, further comprising:
  at least one bladder engagement member that is releasably engageable with the rigid outer body,
  each bladder engagement member, when engaged, compressing at least one of the bladder proximal portion and the bladder distal portion against the rigid outer body to provide a fluid tight seal between the bladder and the rigid outer housing.

Item 26: The compression device of any preceding item, further comprising:
  a proximal bladder engagement member and a distal bladder engagement member, each of the proximal and distal bladder engagement members engageable with the rigid outer body,
  each bladder engagement member, when engaged, compressing a respective one of the bladder proximal portion and the bladder distal portion against the rigid outer body to provide a fluid tight seal between the bladder and the rigid outer housing.

Item 27: The compression device of any preceding item, wherein:
  each bladder engagement member, when engaged, overlies a portion of the rigid outer body and the bladder.

Item 28: The compression device of any preceding item, wherein:
  each bladder engagement member comprises a removable end cap.

Item 29: The compression device of any preceding item, wherein:
  one of the rigid outer body and the bladder comprises a proximal gasket and a distal gasket, and
  each bladder engagement member, when engaged, compresses at least one of the proximal gasket and the distal gasket to provide the fluid tight seal.

Item 30: The compression device of any preceding item, wherein:
  the rigid outer body comprises a proximal gasket underlying the bladder proximal portion, and a distal gasket underlying the bladder distal portion, and
  each bladder engagement member, when engaged, compresses at least one of the proximal gasket and the distal gasket to provide the fluid tight seal.

Item 31: The compression device of any preceding item, wherein:
  each bladder engagement member comprises a gasket that, when the bladder engagement member is engaged, compresses against the bladder.

Item 32: The compression device of any preceding item, wherein:
  each of the bladder proximal portion and the bladder distal portion is folded over an exterior surface of the rigid outer housing.

Item 33: The compression device of any preceding item, further comprising:
  a valve located upstream of the annular inflation chamber, the valve being openable to admit pressurized fluid into the annular inflation chamber, and sealable to seal pressurized fluid in the annular inflation chamber.

Item 34: The compression device of any preceding item, wherein:
  the valve is part of a fluid conduit connector that provides connectivity for an upstream pressurized fluid supply conduit, and the valve is sealable when the fluid conduit connector is disconnected from the upstream pressurized fluid supply conduit.

Item 35: The compression device of any preceding item, wherein:
  the valve automatically seals when the fluid conduit connector is disconnected from the upstream pressurized fluid supply conduit.

Item 36: The compression device of any preceding item, further comprising:
  a user feedback device connected to the rigid outer housing, the user feedback device providing at least one of visual, auditory, and haptic indicia of progress in a digit compression procedure.

Item 37: The compression device of any preceding item, further comprising:
  a user feedback device connected to the rigid outer housing, the user feedback device providing at least one of visual, auditory, and haptic indicia of fluid pressure in the inflation chamber.

Item 38: The compression device of any preceding item, further comprising:
  a controller having one or more processors, and memory storing computer readable instructions that when executed by the one or more processors configure the one or more processors to collectively:
    direct a fluid source to supply fluid through the fluid inlet into the inflation chamber, while directing the fluid source to supply fluid, receive signals indicative of a fluid pressure in the inflation chamber, and direct the fluid source to slow or stop supplying fluid into the inflation chamber in response to determining that the fluid pressure in the inflation chamber has reached a predetermined target pressure.

Item 39: The compression device of any preceding item, wherein the computer readable instructions when executed by the one or more processors configure the one or more processors to collectively:

increment in memory a bladder cycle counter.

Item 40: The compression device of any preceding item, wherein the computer readable instructions when executed by the one or more processors configure the one or more processors to collectively:

direct a user feedback device to provide at least one of visual, auditory, and haptic indicia that a bladder should be replaced, in response to determining that the bladder cycle counter equals or exceeds a predetermined maximum number of cycles.

Item 41: A compression device for freeing a ring trapped on a digit, the compression device comprising:

a rigid outer body extending from a body proximal portion having a body proximal end to a body distal portion having a body distal end, the rigid outer body comprising:
  a digit cavity extending from a cavity proximal opening at the body proximal end to a cavity distal opening at the body distal end, and
  a fluid inlet; and
one or more bladder engagement members collectively having a disengaged position that permits insertion and removal of a flexible tubular bladder through the digit cavity, and an engaged position to seal the flexible tubular bladder extending through the digit cavity to the body proximal and distal portions.

Item 42: The compression device of item 42, further comprising the features of any one or more of items 1-41.

The invention claimed is:

1. A compression device for freeing a ring trapped on a digit, the compression device comprising:
a rigid outer body extending from a body proximal end to a body distal end, the rigid outer body comprising:
  a digit cavity extending from a cavity proximal opening at the body proximal end to a cavity distal opening at the body distal end, and
  a fluid inlet; and
a removable flexible tubular bladder extending from a lining proximal end to a lining distal end, the bladder including a bladder intermediate portion joining a bladder proximal portion to a bladder distal portion, the bladder intermediate portion located inside the digit cavity,
wherein each of the bladder proximal portion and the bladder distal portion are removably sealed to the rigid outer body to define an annular inflation chamber inside the digit cavity between the bladder and the rigid outer body, the fluid inlet being fluidly connected to the annular inflation chamber.

2. The compression device of claim 1, wherein:
the bladder proximal portion overlies the body proximal end, and the bladder distal portion overlies the body distal end.

3. The compression device of claim 1, further comprising:
at least one bladder engagement member that is releasably engageable with the rigid outer body,
each bladder engagement member, when engaged, compressing at least one of the bladder proximal portion and the bladder distal portion against the rigid outer body to provide a fluid tight seal between the bladder and the rigid outer body.

4. The compression device of claim 3, wherein:
each bladder engagement member comprises a removable end cap.

5. The compression device of claim 3, wherein:
each bladder engagement member, when engaged, overlies a portion of the rigid outer body and the bladder.

6. The compression device of claim 3, wherein:
one of the rigid outer body and the bladder comprises a proximal gasket and a distal gasket, and
each bladder engagement member, when engaged, compresses at least one of the proximal gasket and the distal gasket to provide the fluid tight seal.

7. The compression device of claim 3, wherein:
each bladder engagement member comprises a gasket that, when the bladder engagement member is engaged, compresses against the bladder.

8. The compression device of claim 1, wherein:
each of the bladder proximal portion and the bladder distal portion is folded over an exterior surface of the rigid outer body.

9. The compression device of claim 1, further comprising:
a valve located upstream of the annular inflation chamber, the valve being openable to admit pressurized fluid into the annular inflation chamber, and sealable to seal pressurized fluid in the annular inflation chamber.

10. The compression device of claim 9, wherein:
the valve is part of a fluid conduit connector that provides connectivity for an upstream pressurized fluid supply conduit, and the valve is sealable when the fluid conduit connector is disconnected from the upstream pressurized fluid supply conduit.

11. The compression device of claim 10, wherein:
the valve automatically seals when the fluid conduit connector is disconnected from the upstream pressurized fluid supply conduit.

12. The compression device of claim 1, further comprising:
a user feedback device connected to the rigid outer body, the user feedback device providing at least one of visual, auditory, and haptic indicia of progress in a digit compression procedure.

13. The compression device of claim 1, further comprising:
a controller having one or more processors, and memory storing computer readable instructions that when executed by the one or more processors configure the one or more processors to collectively:
  direct a fluid source to supply fluid through the fluid inlet into the inflation chamber,
  while directing the fluid source to supply fluid, receive signals indicative of a fluid pressure in the inflation chamber, and
  direct the fluid source to slow or stop supplying fluid into the inflation chamber in response to determining that the fluid pressure in the inflation chamber has reached a predetermined target pressure.

14. The compression device of claim 13, wherein the computer readable instructions when executed by the one or more processors configure the one or more processors to collectively:
increment in memory a bladder cycle counter.

15. The compression device of claim 14, wherein the computer readable instructions when executed by the one or more processors configure the one or more processors to collectively:
- direct a user feedback device to provide at least one of visual, auditory, and haptic indicia that the bladder should be replaced, in response to determining that the bladder cycle counter equals or exceeds a predetermined maximum number of cycles.

16. The compression device of claim 1, further comprising:
- a proximal bladder engagement member and a distal bladder engagement member, each of the proximal and distal bladder engagement members engageable with the rigid outer body,
- each bladder engagement member, when engaged, compressing a respective one of the bladder proximal portion and the bladder distal portion against the rigid outer body to provide a fluid tight seal between the bladder and the rigid outer body.

17. A compression device for freeing a ring trapped on a digit, the compression device comprising:
- a rigid outer body extending from a body proximal portion having a body proximal end to a body distal portion having a body distal end, the rigid outer body comprising:
  - a digit cavity extending from a cavity proximal opening at the body proximal end to a cavity distal opening at the body distal end, and
  - a fluid inlet; and
- one or more bladder engagement members collectively having a disengaged position that permits insertion and removal of a flexible tubular bladder through the digit cavity, and an engaged position to seal the flexible tubular bladder extending through the digit cavity to the body proximal and distal portions,
- wherein in the engaged position, the flexible tubular bladder defines at least a portion of a tubular inflation chamber inside the digit cavity.

18. The compression device of claim 17, wherein:
the bladder comprises a bladder proximal portion and a bladder distal portion, and
when the one or more bladder engagement members are collectively in the engaged position, the bladder proximal portion overlies the body proximal end, and the bladder distal portion overlies the body distal end.

19. The compression device of claim 17, wherein:
the bladder comprises a bladder proximal portion and a bladder distal portion, and
each bladder engagement member, when engaged, compressing at least one of the bladder proximal portion and the bladder distal portion against the rigid outer body to provide a fluid tight seal between the bladder and the rigid outer body.

20. A compression device for freeing a ring trapped on a digit, the compression device comprising:
- a rigid outer body extending from a body proximal portion having a body proximal end to a body distal portion having a body distal end, the rigid outer body comprising:
  - a digit cavity extending from a cavity proximal opening at the body proximal end to a cavity distal opening at the body distal end,
  - a fluid inlet;
- a removable flexible tubular bladder extending through the digit cavity, the bladder defining at least a portion of an annular inflation chamber inside the digit cavity; and
- a controller having one or more processors, and memory storing computer readable instructions that when executed by the one or more processors configure the one or more processors to collectively:
  - direct a fluid source to supply fluid through the fluid inlet into the inflation chamber,
  - while directing the fluid source to supply fluid, receive signals indicative of a fluid pressure in the inflation chamber, and
  - direct the fluid source to slow or stop supplying fluid into the inflation chamber in response to determining that the fluid pressure in the inflation chamber has reached a predetermined target pressure.

* * * * *